US012195761B2

(12) United States Patent
Schmidt et al.

(10) Patent No.: US 12,195,761 B2
(45) Date of Patent: Jan. 14, 2025

(54) BIOPRINTED, 3D SCAFFOLDS FOR CELLULAR TEST BEDS AND METHODS OF USE THEREOF

(71) Applicant: University of Florida Research Foundation, Inc., Gainesville, FL (US)

(72) Inventors: Christine E. Schmidt, Gainesville, FL (US); Benjamin Scott Spearman, Tampa, FL (US); Tran Ngo, Bethesda, MD (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 207 days.

(21) Appl. No.: 17/236,352

(22) Filed: Apr. 21, 2021

(65) Prior Publication Data

US 2021/0324336 A1 Oct. 21, 2021

Related U.S. Application Data

(60) Provisional application No. 63/013,443, filed on Apr. 21, 2020.

(51) Int. Cl.
*C12N 5/071* (2010.01)
*C12N 5/0775* (2010.01)
*G01N 33/50* (2006.01)

(52) U.S. Cl.
CPC ......... *C12N 5/0671* (2013.01); *C12N 5/0667* (2013.01); *C12N 5/0668* (2013.01); *C12N 5/0691* (2013.01); *C12N 5/0697* (2013.01); *G01N 33/5026* (2013.01); *G01N 33/5082* (2013.01); *C12N 2500/25* (2013.01); *C12N 2500/32* (2013.01); *C12N 2501/135* (2013.01); *C12N 2501/15* (2013.01); *C12N 2501/165* (2013.01); *C12N 2533/54* (2013.01); *C12N 2533/74* (2013.01); *G01N 2500/10* (2013.01)

(58) Field of Classification Search
CPC ............... C12N 5/0671; C12N 5/0667; C12N 5/0668; C12N 5/0691; C12N 5/0697; C12N 2500/25; C12N 2500/32; C12N 2501/135; C12N 2501/15; C12N 2501/165; C12N 2533/54; C12N 2533/74; G01N 33/5026; G01N 33/5082; G01N 2500/10

See application file for complete search history.

(56) References Cited

U.S. PATENT DOCUMENTS 10,273,549 B2    4/2019   Helgason et al.
2017/0276668 A1  9/2017   Curley et al.

FOREIGN PATENT DOCUMENTS

WO   WO-2018071354 A1 *  4/2018  ............ C12M 21/08

OTHER PUBLICATIONS

Spearman, B. S., et al., "Tunable methacrylated hyaluronic acid-based hydrogels as scaffolds for soft tissue engineering applications," Journal of Biomedical Materials Research Part A 108(2): 279-291. doi: 10.1002/jbm.a.36814. Epub Oct. 29, 2019. (Year: 2019).*
D'Amora, U., et al., "In situ sol-gel synthesis of hyaluronan derivatives bio-nanocomposite hydrogels," Regenerative Biomaterials 6(5): 249-258. doi: 10.1093/rb/rbz029. Epub Oct. 9, 2019. (Year: 2019).*
Levett, P. A., et al., "Chondrocyte redifferentiation and construct mechanical property development in single-component photocrosslinkable hydrogels," J Biomed Mater Res A 102(8): 2544-2553. doi: 10.1002/jbm.a.34924. Epub Sep. 2, 2013. (Year: 2013).*
Ouyang et al., 2016a. "3D Printing of Shear-Thinning Hyaluronic Acid Hydrogels with Secondary Cross-Linking." ACS Biomater, Sci. Eng. 2, 1743-1751, https://doi.org/10.1021/acsbiomaterials.6b00158.
Poldervaart et al., 2017. "3D bioprinting of methacrylated hyaluronic acid (MeHA) hydrogel with intrinsic osteogenicity", PLoS One 12, 1-15, https://doi.org/10.1371/journal.pone.0177628.
Yu et al., 1999. "A laminin and nerve growth factor-laden three-dimensional scaffold for enhanced neurite extension", Tissue Eng. 5, 291-304. https://doi.org/10.1089/ten.1999.5.291.
Noh et al., "3D printable hyaluronic acid-based hydrogel for its potential application as a bioink in tissue engineering" Biomaterials Research, 2019, 23:3, pp. 1-9. https://doi.org/10.1186/s40824-018-0152-8.
Lampe, et al., "Design of Three-Dimensional Engineered Protein Hydrogels for Tailored Control of Neurite Growth", Acta Biomater. 2013, 9 (3), 5590-5599. https://doi.org/10.1016/j.actbio.2012.10.033.
Suri, et al., "Photopatterned Collagen-Hyaluronic Acid Interpenetrating Polymer Network Hydrogels", Acta Biomater. 2009, 5 (7), 2385-2397. https://doi.org/10.1016/j.actbio.2009.05.004.
Kiyotake, et al., "Development and Quantitative Characterization of the Precursor Rheology of Hyaluronic Acid Hydrogels for Bioprinting", Acta Biomater. 2019, 95, 176-187. https://doi.org/10.1016/j.actbio.2019.01.041.
Mazzocchi et al., "Optimization of Collagen Type I-Hyaluronan Hybrid Bioink for 3D Bioprinted Liver Microenvironments", Biofabrication 2019, 11, 15003. https://doi.org/10.1088/1758-5090/aae543.
Gomez, et al., "Polarization of Hippocampal Neurons with Competitive Surface Stimuli: Contact Guidance Cues Are Preferred over Chemical Ligands", J. R. Soc. Interface 2007, 4 (13), 223-233. https://doi.org/10.1098/rsif.2006.0171.

* cited by examiner

*Primary Examiner* — Tracy Vivlemore
*Assistant Examiner* — Eric J Rogers
(74) *Attorney, Agent, or Firm* — Thomas| Horstemeyer LLP

(57) ABSTRACT

The disclosure provides 3D bioprinted test beds and methods of making the 3D bioprinted teste beds, methods of using the 3D bioprinted test beds for testing and/or comparatively testing two or more test compounds on cell growth and/or behavior, as well as biocompatible methacrylated hyaluronic acid-based bioinks for printing the 3D test beds and/or other articles. The 3D test beds and bioinks include a hydrogel material/precursor and can include extracellular matrix components.

15 Claims, 7 Drawing Sheets

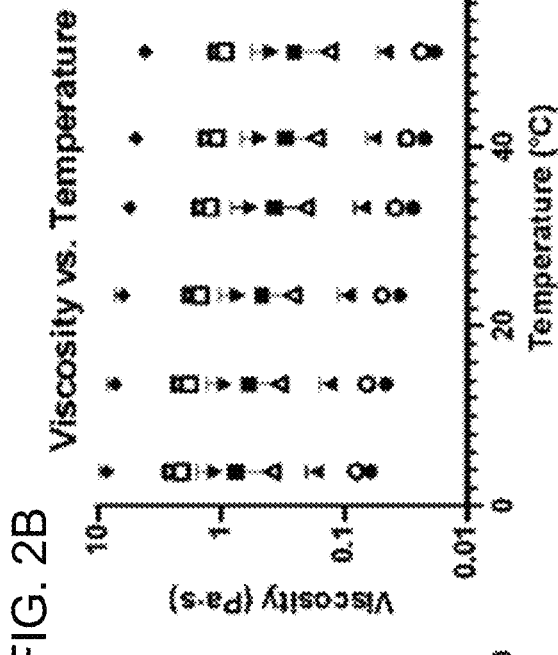
FIG. 2A
FIG. 2B
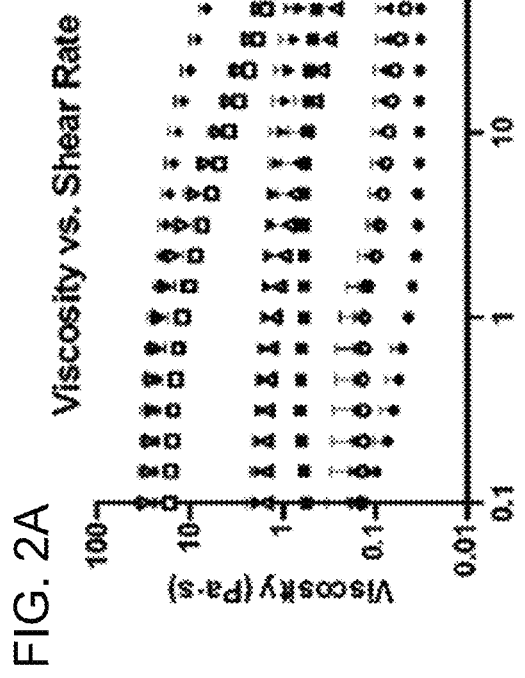
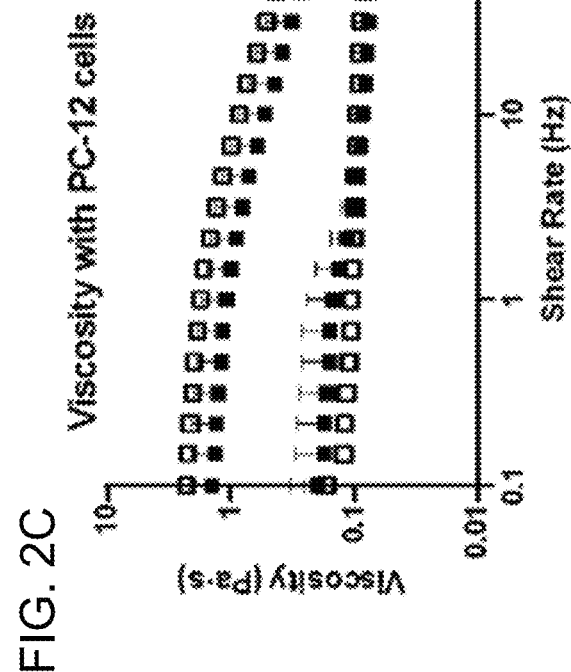
FIG. 2C

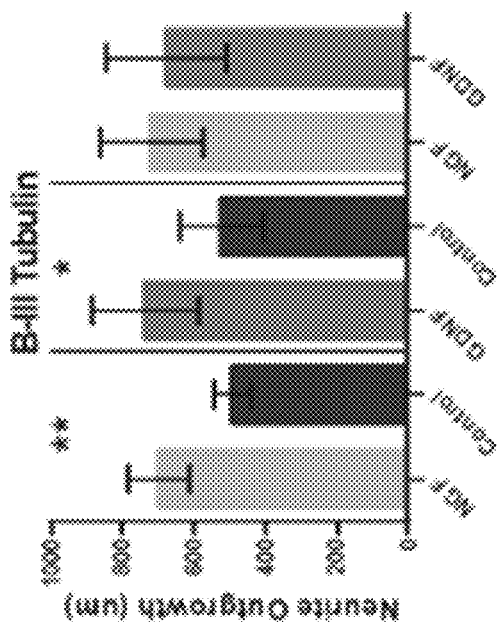
FIG. 6D FIG. 6E FIG. 6F
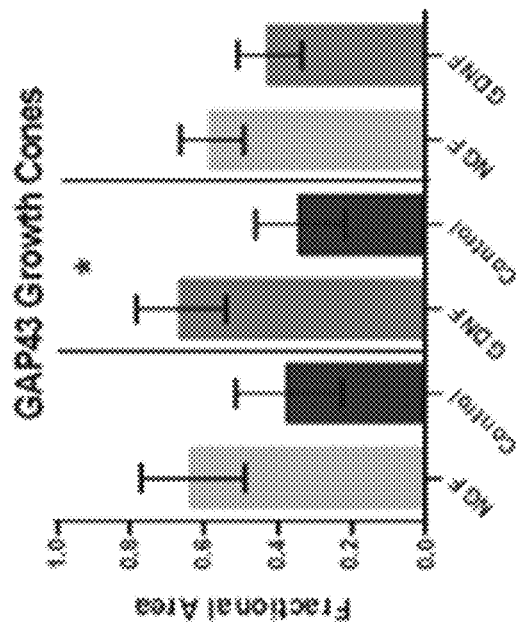
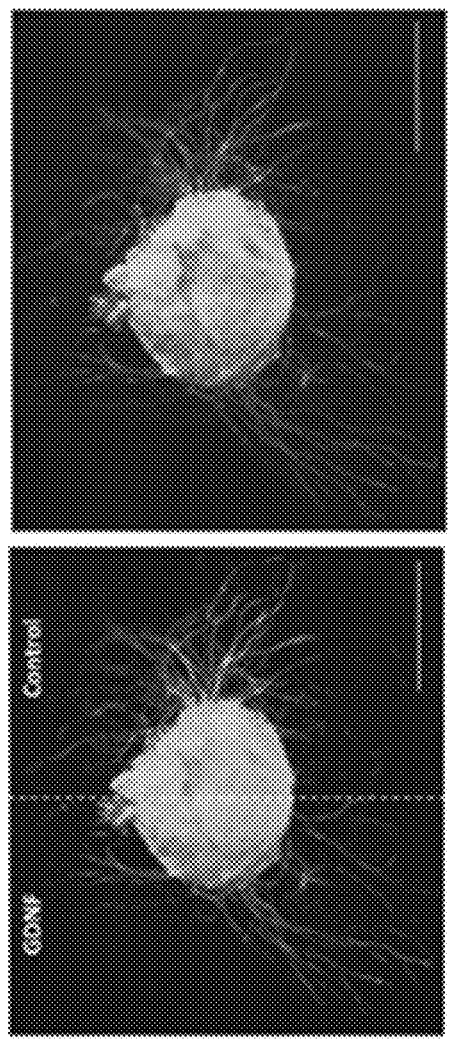
FIG. 6G FIG. 6H FIG. 6I
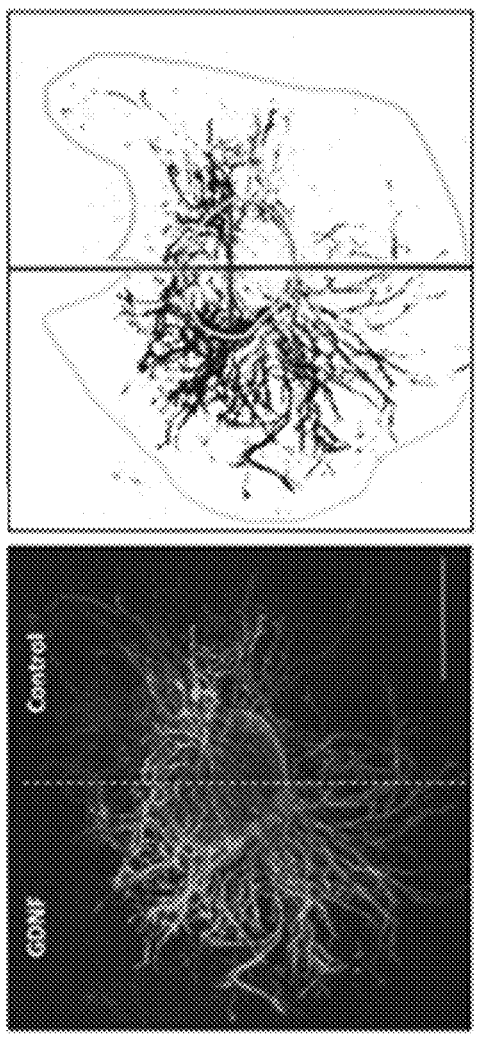

BIOPRINTED, 3D SCAFFOLDS FOR CELLULAR TEST BEDS AND METHODS OF USE THEREOF

CROSS-REFERENCE TO RELATED APPLICATIONS

This application claims the benefit of and priority to U.S. Provisional Patent Application No. 63/013,443, filed on Apr. 21, 2020, entitled "BIOPRINTED, 3D SCAFFOLDS FOR CELLULAR TEST BEDS AND METHODS OF USE THEREOF," the contents of which is incorporated by reference herein in its entirety.

BACKGROUND

Developments in three dimensional (3D) bioprinting provide new applications for tissue engineering. With bioprinting, tissue engineers create custom 3D tissue-engineered constructs to serve a variety of purposes. Long-term, one of the primary goals of bioprinting is to be able to print fully customized 3D tissues, and perhaps full organs, containing relevant cell types, extracellular matrix, and vasculature. Another application of 3D bioprinting is development of advanced in vitro test beds and models. In vivo studies and tests provide important and necessary information for certain biomedical devices and pharmaceuticals, but these in vivo models present various challenges, such as ethical concerns, cost, and questionable translatability. Although 3D bioprinting offers promise for creation of customizable in vitro models, the current lack of suitable models for nerve growth and the print quality limitations of available bioinks hinder the printing of high-quality 3D models in bioprinters, such as extrusion based bioprinters.

SUMMARY

In various aspects described herein, 3D bioprinted test beds, methods of making the 3D bioprinted test beds, methods of using the test beds for comparative testing of test compounds, and biocompatible methacrylated hyaluronic acid-based bioink compositions are provided.

In some aspects described herein, the bioink for printing the 3D test beds and scaffolds of the present disclosure includes a MeHA compound and extracellular matrix (ECM) component, a biocompatible photoinitiator capable of crosslinking the MeHA compound and the ECM component to create a hydrogel.

The present disclosure provides 3D bioprinted test beds including a central section comprising a base hydrogel material and living cells printed within the base material; a first arm portion comprising the base hydrogel material and a first test compound printed within the base material; and a second arm portion comprising the base hydrogel material and, optionally, a second test compound, other test stimulus, or a combination thereof, printed within the base material. According to some aspects, the base hydrogel material comprises a biocompatible hydrogel matrix material that provides a stable 3D hydrogel scaffold and wherein the base hydrogel material optionally further comprises an extracellular matrix (ECM) component crosslinked with the hydrogel material to create a stable 3D hydrogel scaffold.

Other aspects of the present disclosure include 3D bioprinted cell scaffolds including a multi-component methacrylated hyaluronic acid (MeHA)-based hydrogel, where the hydrogel includes an MeHA component and an extracellular matrix (ECM) component, the MeHA component and ECM component crosslinked to create a stable 3D hydrogel scaffold. According to aspects, the scaffold further includes at least one population of living cells seeded within the 3D hydrogel scaffold and one or more optional test compounds where the cells and test compounds are located in the same or different portions of the cell scaffold.

According to other aspects of the present disclosure, methods of making 3D bioprinted test beds are provided. Such methods include:

a. providing a base bioink composition comprising a multi-component methacrylated hyaluronic acid (MeHA)-based hydrogel precursor composition comprising a MeHA component, an extracellular matrix (ECM) component, and a photoinitiator capable of crosslinking the MeHA component and the ECM component;

b. optionally combining one or more additional components with the base bioink composition to form one or more combined bioink compositions, wherein additional components are selected from the group consisting of: living cells, test compounds, growth factors and growth media;

c. loading the base bioink composition or combined bioink composition in an extrusion-based 3D bioprinter and allowing partial gelation of the bioink before printing;

d. printing at least a central portion of the 3D bioprinted test bed;

e. repeating steps c-d as needed to print the 3D bioprinted test bed comprising at least a central portion, at least a first and second arm portion, and any optional additional arm portions, wherein each portion may be printed with the same or different base bioink composition or combined bioink compositions and wherein each portion may be printed from different nozzles of the 3D bioprinter or from separate printers; and f. exposing the printed 3D bioprinted test bed to UV light to crosslink the MeHA component and ECM component to create a stable 3D hydrogel scaffold In further aspects, the present disclosure provides methods of comparatively testing the effect of two or more test compounds on cell growth behavior, such methods including: providing a 3D bioprinted test bed of the present disclosure, wherein the cells are in the central portion and wherein the first arm portion contains a test compound and the second arm portion contains a second test compound a test stimulus or no additional test compounds or stimuli; culturing the 3D bioprinted test bed; and quantitatively comparing cell growth behavior of cells in the central portion towards each arm portion to determine if each test compound has a positive or negative affect on one or more cell growth behaviors. In embodiments cell growth behaviors can be selected from at least the following: cell growth, cell proliferation, cell migration, and neurite extension, measurement of secreted protein products, measurement of cellular electrical activity, and measurement of protein/gene expression.

Other systems, methods, features, and advantages of the 3D bioprinted test beds, bioink compositions, and methods of making and using the 3D bioprinted test beds will be apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings. The components in the drawings are not necessarily to scale, emphasis instead being placed upon clearly illustrating the principles of the present disclosure. Moreover, in the drawings, like reference numerals designate corresponding parts throughout the several views.

FIGS. 2A-2C are graphs illustrating rheological characterization of various MeHA bioink compositions. FIG. 2A shows viscosity relative to shear rate, FIG. 2B shows viscosity relative to temperature.

FIGS. 3A-3D illustrate printability scores of various methacrylated HA hydrogels that were tested. FIG. 3A is a graph of original printability scores found by determining the circularity of each printed square, FIG. 3B graphs the fraction of squares successfully printed, and FIG. 3C is a graph of adjusted printability scores derived from multiplying the printability score by the fraction of printed squares. D) Example prints (10 mm length, 10 mm width and 1.2 mm height), sorted by adjusted printability score. Scale bars=2 mm. ****ANOVA p-value<0.0001.

FIG. 4A is a graph illustrating average intensity for integrin β1 of SCs cultures in MAHA 10/Col-I indicated 85.4±3.6 percent, which is significantly less than of the purely adhesive Col-d gels (n=4). FIG. 4B illustrates that the area of positive signal per cell also indicated a significant decrease for MAHA 10/Col-I compared to Col-d alone (n=4). FIG. 4C illustrates that the percent area (total coverage), indicated a significant global increase of integrin β1 expression in SC cultured in MAHA 10/Col-I (n=4). * p≤0.05.

FIGS. 6A-6I illustrate 3D bioprinted test beds and use of the test beds for a competitive assay of growth factors NGF and GDNF vs each other and control. FIG. 6A is a schematic of a competitive 3D bioprinted test bed in the slicer software used, Cellink HeartWare, indicating nozzle travel paths. FIG. 6B is an image of an early test print of DRG test bed using MAHA 10 mg/mL with food coloring to differentiate prints from separate nozzles (scale bar=3 mm). FIG. 6C is an image of a final test bed print before DRG seeding. FIG. 6D illustrates quantification of DRG neurite extensions (β-III tubulin) within the 3D bioprinted DRG test bed. An example of a top view confocal image of a DRG using maximum intensity projection, showing directional neurite extensions. FIG. 6E illustrates an example of neurite outlined using the neurite tracer function on ImageJ. FIG. 6F is a graph of direct comparisons of neurite lengths within the same test bed including NGF/control, GDNF/control, and NGF/GDNF (n=5). FIG. 6G illustrates GAP 43 quantification of DRG neural growth cone within the 3D bioprinted DRG test bed. An example of a DRG image showing directional neuronal growth signal toward GDNF chamber. FIG. 6H illustrates an example of GAP43-positive signal quantification. FIG. 6I graphs direct comparisons of GAP43 signal within the same test bed including NGF/control, GDNF/control, and NGF/GDNF (n=3). Scale bars=500 µm. **p≤0.01, *p≤0.05.

DETAILED DESCRIPTION

Figure 1:
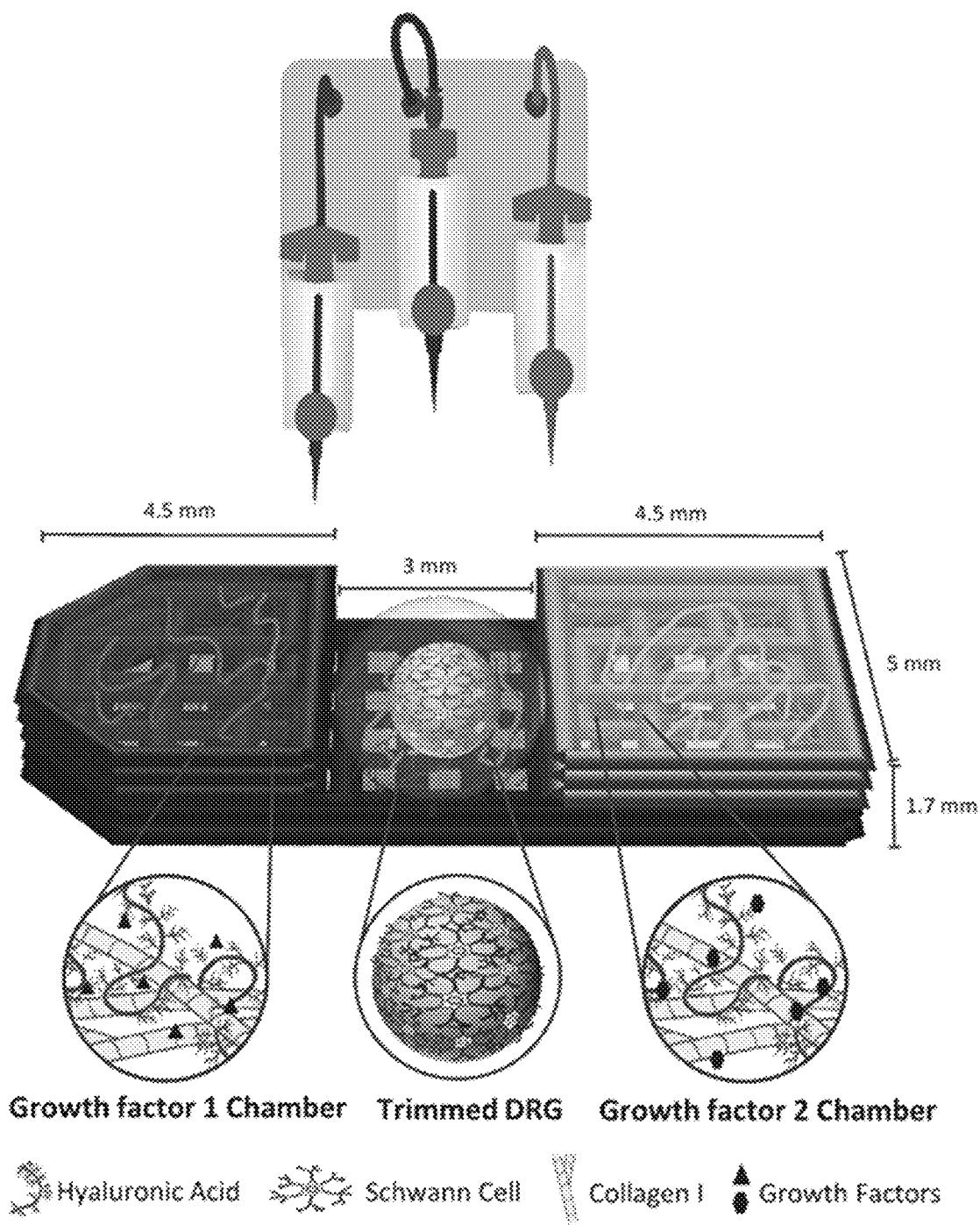
FIG. 1 is a schematic illustration of an embodiment of a 3D bioprinted in vitro test bed design including a base printing with the main bioink and two chambers or "arms" that can be loaded with different growth factors or other test compounds/stimuli. A trimmed DRG is shown seeded in Col-d glue at the center of the design.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of biochemistry, material science, biology, molecular biology, and the like, which are within the skill of the art. Such techniques are explained fully in the literature.

The following examples are put forth to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20-25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

All publications and patents cited in this specification are cited to disclose and describe the methods and/or materials in connection with which the publications are cited. Publications and patents that are incorporated by reference, where noted, are incorporated by reference as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. Any terms not specifically defined within the instant application, including terms of art, are interpreted as would be understood by one of ordinary skill in the relevant art; thus, is not intended for any such terms to be defined by a lexicographical definition in any cited art, whether or not incorporated by reference herein, including but not limited to, published patents and patent applications. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

It must be noted that, as used in the specification and the appended claims, the singular forms "a," "an," and "the" include plural referents unless the context clearly dictates otherwise. Thus, for example, reference to "a cell" includes a plurality of cells. In this specification and in the claims that follow, reference will be made to a number of terms that shall be defined to have the following meanings unless a contrary intention is apparent.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing and claiming the disclosed subject matter, the following terminology will be used in accordance with the definitions set forth below.

As used herein, "about," "approximately," and the like, when used in connection with a numerical variable, generally refers to the value of the variable and to all values of the variable that are within the experimental error (e.g., within the 95% confidence interval for the mean) or within +/−10% of the indicated value, whichever is greater.

As used herein, the terms "optional" or "optionally" means that the subsequently described event or circumstance can or cannot occur, and that the description includes instances where said event or circumstance occurs and instances where it does not.

As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed. In embodiments a "test compound" may be or include an "active agent."

As used herein, the term "biocompatible" refers to the ability to co-exist with a living biological substance and/or biological system (e.g., a cell, cellular components, living tissue, organ, etc.) without exerting undue stress, toxicity, or adverse effects on the biological substance or system. With respect to a substance or structure described herein "biocompatible" can also indicate that the substance or structure does not adversely affect the short-term viability or proliferation of living cells within or on the substance/structure.

The term "scaffold," "scaffold material," "cell scaffold" or "cell migration scaffold" refers to any compound substance with sufficient structural stability to provide a substrate to support the growth of a living biological substance (e.g., living cells). In embodiments of the present disclosure, a biocompatible scaffold material has a three-dimensional structure (rather than a planar, 2-dimensional structure) to support three-dimensional growth of living cells. In embodiments, the biocompatible scaffold material is made from a liquid/semi-liquid material that can be crosslinked and/or polymerized into a matrix that provides a more solid support network (e.g., solid, gel, semi-solid, hydrogel, etc.).

The term "matrix material" refers to several different types of semi-solid to solid materials with a gel-like and/or solid consistency and a structure capable of supporting the growth of living biological substances (e.g., living cells). Gel matrix materials include hydrogels, such as biocompatible naturally derived or synthetic hydrogels, such as, but not limited to HA-based hydrogels, multi-component HA-based hydrogels, MeHA hydrogels, collagen, laminin, combinations of these hydrogel materials, and the like. Gel matrix materials may also include a gelling agent or crosslinking agent (e.g., photoinitiator or other cross-linking agent, etc.) to increase the structural stability of the gel (e.g., to give it more "solid" characteristics).

The term "cell migration scaffold" refers to a biocompatible scaffold of the present disclosure that is configured for observation, analysis, and testing of cell properties and behavior and cell growth and migration within the scaffold, including assays of cell migration in general or in response to a specific stimuli.

The term "test bed" as used herein refers to a scaffold, such as scaffolds of the present disclosure, that is configured to allow biocompatible, in vitro competitive/comparative testing of one or more or two or more test compounds for certain effects on a living system, such as living cells, cell functions, features, and the like. For instance, a test bed may provide a comparative assays such as, but not limited to: a test compound vs. a control (neutral, positive, and/or negative control), test compound vs. another test compound, test compound vs a control and one or more other test compounds, and the like.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents and are meant to include future updates.

Further definitions may be provided in context below. Unless otherwise defined, all technical and scientific terms used herein have the same meaning as commonly understood by one of ordinary skill in the art of material science and/or molecular biology. Although methods and materials similar or equivalent to those described herein can be used in the practice or testing of the present disclosure, suitable methods and materials are described herein.

Discussion

In accordance with the purpose(s) of the present disclosure, as embodied and broadly described herein, embodiments of the present disclosure, in some aspects, relate to methacrylated hyaluronic acid (MeHA) bioinks; 3D bioprinted, multi-component, biocompatible hydrogel cell migration scaffolds and/or test beds; devices/kits including the biocompatible hydrogel scaffolds/test beds of the present disclosure, and methods for making the 3D bioprinted, biocompatible hydrogel scaffolds/test beds of the present disclosure, and the like. The present disclosure also includes methods for performing a competitive assay to compare the effects of one or more test compounds on cell migration and/or cell growth, such as, but not limited to neural extension growth, using the hydrogel scaffolds/test beds of the present disclosure. Advantages and features of the bioinks, scaffolds/test beds, methods, devices, and kits of the present disclosure will be explained in greater detail in the description and examples below.

The use and development of advanced in vitro models reduces the use of animal research and provides several potential advantages over the use of animal models. First, it reduces or eliminates many ethical considerations over the use of animals. Second, compared to the high costs associated with animal research, in vitro test bed models are more cost effective. Third, in vitro test beds have the potential to provide fully customizable treatments for specific patients. Such customized treatments may involve continued development of induced pluripotent stem cells, but a robust in vitro model has the potential to use a patient's own cells to test competitive treatment options and find what will work best for each individual. While translatability is still a concern with any in vitro test, this increased customizability to the patient is a huge advantage to these models.

In the field of nerve tissue engineering, there is a dearth of suitable in vitro peripheral nerve test beds. The complete customizability of 3D bioprinting provides promising avenues to develop a suitable platform for developing nervous tissue test beds and test beds for other tissue and cell types. In nerve tissue engineering, the most commonly used in vitro tests include standard 2D cell culture with relevant cell types (e.g., Schwann cells, various neural cell lines such as PC-12 cells, and the like) or basic culture of neonatal dorsal root ganglia (DRG) explants. Development of peripheral nerve test beds can reduce the number of animals used in this field while utilizing the inherent advantages of test bed technologies, as discussed above.

Hyaluronic acid (HA) is a widely used material in tissue engineering and is a suitable material for the development of peripheral nerve in vitro test beds. HA is found in a wide variety of tissues, is highly modifiable, and plays a known role in various regenerative processes, including in the nervous system. This makes HA an attractive material for use as a bioink. However, there are certain limitations for deciding what bioink to use with extrusion-based bioprinters, such as the CELLINK BIO X™ printer that was used for the following studies. A bioink for use with extrusion-based bioprinters must meet certain requirements. For instance, high viscosity with shear thinning properties is preferred. Shear thinning allows the bioinks to be easily extruded while the high viscosity will help the material hold its shape until crosslinked. Shear thinning also has a protective effect on cells printed with extrusion-based bioprinting. Quick crosslinking is also desirable so that the shape of the print can be "locked" into place before the printed bioink loses its shape.

With all of this in mind, the properties of methacrylated hyaluronic acid (MeHA) make it difficult to translate for use in bioprinting. While the pre-hydrogel solution viscosity can vary greatly, the higher viscosity solutions can be difficult to dissolve. However, the bioinks of the present disclosure overcome these drawbacks and provide desirable properties for bioprinting 3D scaffolds suitable for use as cell migration scaffolds and/or test beds for cell migration assays and/or neurite extension assay.

Biocompatible Bioinks

Embodiments of the present disclosure include a biocompatible bioink composition that can be used to make 3D bioprinted test beds and scaffolds according to the present disclosure. The bioink can include hydrogel precursor compounds, such as methacrylated hyaluronic acid (MeHA)-based compositions, extracellular matrix materials, and/or other biocompatible materials suitable for bioprinting applications, and combinations of these materials. In embodiments, the bioink is a base hydrogel material or precursor material that can include a biocompatible hydrogel matrix material capable of curing/crosslinking to provide a stable 3D hydrogel scaffold. The base hydrogel material can also include an optional extracellular matrix (ECM) component crosslinked with the hydrogel material to create a stable 3D hydrogel scaffold. In embodiments the bioink is a biocompatible, multi-component MeHA-based bioink composition including at least one MeHA compound(s), an extracellular matrix (ECM) component, and a biocompatible crosslinking initiator (e.g., a photoinitiator) capable of crosslinking the MeHA compound(s) and the ECM component to create a hydrogel.

The MeHA compound(s) can include compounds, such as, but not limited to: glycidyl methacrylate HA (GMHA), methacrylic anhydride HA (MAHA), as well as combinations of the above materials. The MeHA-based composition can have a degree of methylation of about 2.4 to 86%. In embodiments, the MeHA composition has a degree of methylation of 10% or greater, which allows suitable printing of the material. In embodiments, the degree of methylation is about 30% or greater. In embodiments, the MeHA compound can be GMHA, MAHA, or a combination of these having a concentration of about 10-40 mg/mL. For example, the MeHA compound can be MAHA having a concentration of about 10-20 mg/mL, such as MAHA having a concentration of about 10 mg/ML (MAHA 10).

In embodiments, the ECM component can be, but is not limited to: collagen (e.g., collagen I, collagen II, collagen III, collagen IV, etc.), laminin, or a combination thereof. The ECM material can be from a mammal, such as, but not limited to human, bovine, porcine, murine, or other organism such as rabbits or goats. In embodiments, the ECM component is collagen (e.g., collagen I, collagen II, etc.) having a concentration of about 0.1-50 mg/mL. In embodiments, the collagen has a concentration of about 1-5 mg/mL. In a particular embodiment, the MeHA compound is MAHA 10 and the ECM component is collagen I.

The bioink also can also include an initiator that, upon application of a certain stimulus, initiates crosslinking of the MeHA and/or other base hydrogel precursor compound and the ECM component to create a hydrogel. In embodiments the initiator is a photoinitiator capable of initiating crosslinking upon application of UV light. The initiator can be a photoinitiator, such as, but not limited to, lithium phenyl-2, 4,6-trimethylbenzoylphosphinate (LAP), 2-Hydroxy-4'-(2-hydroxyethoxy)-2-methylpropiophenone (Irgacure™ 2959 or I2959), or other biocompatible photoinitiators. The bioink composition can also include additional components prior to printing, such as, but not limited to, living cells (of one or more types), growth factors, culture media, test compounds (e.g., growth factors, drugs, other bioactive agents, and the like). In embodiments, the bioink can include cells and other compounds needed to sustain viability of the cells (such as nutrients, growth factors, etc.).

In embodiments, the components of the bioink can partially crosslink prior to application of the initiator stimulus. For instance, the components can partially crosslink or gel upon combination, incubation, and the like. In some embodiments, the bioink is partially gelled (e.g., by incubation in the bioprinter) prior to printing in order to increase the viscosity and structural integrity of the resulting printed material. In embodiments, the bioink composition has an initial viscosity of about 1 to 100 Pa·s (e.g., at the time of initial combination). The bioink can have a printing viscosity of 10 to 1,000 Pa·s at the time of printing. In embodiments, after printing, the initiator stimulus can be applied (e.g., UV light) to the printed material to initiate final crosslinking of the printed form to create a 3D structure (e.g., scaffold, test bed, etc.).

3D Bioprinted Test Beds and Scaffolds

The present disclosure also provides 3D bioprinted test beds, such as test beds made with the biocompatible bioink of the present disclosure described above. The 3D bioprinted test beds include at least: a central section, a first arm portion, and a second arm portion. The central section is made of a base hydrogel material and can have living cells printed within the base material. The first arm portion also includes a base hydrogel material and a first test compound printed within the base material. The second arm portion includes the base hydrogel material and an optional second test compound printed within the base material.

The base hydrogel material is a multi-component biocompatible hydrogel material that includes two or more biocompatible hydrogel/matrix materials. The base hydrogel material can be a crosslinked hydrogel bioink of the present disclosure described above. In embodiments, the base hydrogel material is a multi-component methacrylated hyaluronic acid (MeHA)-based hydrogel. The multi-component MeHA based hydrogel can include a MeHA component and an extracellular matrix (ECM) component, where the MeHA and ECM components are crosslinked to create a stable 3D hydrogel scaffold. In embodiments, the MeHA compound is selected from glycidyl methacrylate HA (GMHA), methacrylic anhydride HA (MAHA), or a combination thereof, having a concentration of 10-40 mg/mL (e.g., MAHA 10). The ECM component can be, but is not limited to: collagen, laminin, or a combination thereof. In embodiments, the ECM is collagen and has a concentration of about 0.1-50 mg/mL. In some embodiments, the collagen has a concentration of about 1-5 mg/mL. The collagen can be, but is not limited to collagen I, collagen II, collagen III, collagen IV, a combination thereof, etc. In an embodiment, the multi-component MeHA based hydrogel includes MAHA having a concentration of about 10-20 mg/mL and collagen as the ECM component and having a concentration of about 0.1-50 mg/mL.

The base hydrogel material can also include other materials to sustain the viability of living cells printed within the base material, such as, but not limited to nutrients, growth factors, and the like, such as would be included in a suitable growth medium. The composition of the base hydrogel material in the central portion and each of the first arm portion and second arm portion can differ somewhat. For instance, while the base hydrogel material for all portions of the test bad can have the same MeHA based hydrogel and ECM component, the base material in each arm portion may differ in the presence of test compounds, growth factors, nutrients and the like. In embodiments, the test compounds can be independently chosen from compounds and/or combinations of compounds, such as, but not limited to: growth factors, bioactive agents (e.g., small molecule drugs, biomolecules such as proteins, peptides, polynucleotides, etc.), nutrients, and the like) or other chemical stimuli capable of being printed with or applied in the base hydrogel material of the test arm portion.

The different arms of the test bed can each include different test compounds (or the first arm includes a test compound and the second arm contains no test compounds (e.g., control)) such that the growth/migration of cells from the central portion of the test bed toward the different arms of the test bed can be monitored to determine the effect of a test compound on the cells in the central portion. In embodiments, other test stimuli can also be used instead of or in combination with a test compound. One such test stimulus can include physical stimuli, such as but not limited to, microarchitectural features in the test bed structure or base hydrogel mixtures of varying mechanical properties (such as varying density, viscosity, different base materials, or the presence of additional materials). Another test stimulus can include the presence of support cells, other living cells that may foster or inhibit growth for the primarily cells being tested in the central section (e.g. Schwann cells which are support cells for the peripheral nervous system). Other test stimuli could include forces, such as applied electrical, mechanical, or chemical forces. It is contemplated that in most embodiments, at least one arm portion of the test bed will include a test stimulus that can be printed with the base hydrogel material within the arm portion of the test bed, such as a test compound or other chemical stimulus. In embodiments the test bed is a competitive test bed designed to test the competitive effect of two or more different test compounds (and/or test stimuli) on cells in the central portion of the test bed. In such embodiments, different test compounds (and/or other test stimuli) are printed in at least the first arm portion and second arm portion of the test bed.

Although it is contemplated that the 3D bioprinted test beds of the present disclosure can be used to test various cell types (e.g., nervous tissue cell, muscle cells, endothelial cells, skeletal cells, fat cell, tumor cells, etc.) and/or tissue types, in some exemplary embodiments of the present disclosure, the 3D bioprinted test beds are designed for testing the effect of various test compounds (and/or test stimuli) on the growth of neural cells. Thus, in such embodiments, the cells printed within the base material in the central portion are neural cells (e.g., dorsal root ganglia). The cells can have an initial density (at or just prior to printing) of about $10^4$ to $10^7$ cells/mL. In some embodiments, the first and second arm portions (and/or additional arm sections) do not initially have any cells printed in the base material. However, when used, the cells initially printed in the central portion may migrate, grow, or proliferate towards and/or into one or more of the arm portions. In embodiments, where dorsal root ganglia are used, the cells may exhibit neurite outgrowth, and such neurite outgrowth may be greater (qualitatively and/or quantitatively (e.g., number of neurites or length)) towards one arm or another, due to, for instance, the presence of a test compound or other test stimulus in such arm portion.

Some 3D bioprinted test beds of the present disclosure can include one or more additional arm portion, where each additional arm portion can have a different test compound or other test stimulus than the first and second arm, or a different combination of test compounds and/or test stimuli. In an embodiment, the central portion may have multiple arms radiating out from the center (e.g., an asterisk or octopus-type shape). Each arm of the multi-arm test bed can have a different test compound/stimulus or combination, and optionally one of the arms may not have a test compound/ stimulus, e.g., a control arm.

In addition to the test beds described above, the present disclosure also contemplates that these materials and methods of the present disclosure can be used to provide 3D bioprinted scaffolds for cells/tissues. The 3D cell (or tissue) scaffolds of the present disclosure can include the biocompatible hydrogel materials described above. In embodiments, the 3D bioprinted cell scaffolds include a multi-component MeHA based hydrogel, where the hydrogel includes at least an MeHA component and an ECM component, where the components have been combined as a bioink and printed into a 3D structure and crosslinked to create a stable 3D hydrogel scaffold. The 3D bioprinted scaffolds can also include at least one population of living cells seeded within the 3D hydrogel scaffold (for instance, the cells can be combined with the bioink and printed with the scaffold). The 3D bioprinted scaffolds of the present disclosure can also include one or more optional growth compounds, test compounds, growth medium, or other materials, such as describe above. The cells and the test compounds can be located in different portions of the cell scaffold or the same portion.

Methods of Making 3D Bioprinted Test Beds

The present disclosure also provides methods of making the 3D bioprinted test beds and/or cell scaffolds of the present disclosure. The methods include providing a base bioink composition (such as those described above including at least a biocompatible hydrogel and an initiator compound), optionally combining the base bioink composition with one or more additional components (such as, but not limited to, living cells, test compounds, test stimuli, growth factors and growth media) to form a combined bioink composition, loading the base bioink or combined bioink composition into an extrusion-based 3D bioprinter, and printing at least a central portion of the 3D bioprinted test bed or portion of a cell scaffold. After loading the bioink or combined bioink composition into the bioprinter, optionally, the bioink can be allowed to partially gel (e.g., due to incubation for a length of time or at an elevated temperature, or both) prior to printing to improve the printability and stability of the bioink between printing and final crosslinking.

The steps of loading the bioink into the printer and printing can be repeated as needed to print different portions of the 3D test bed and/or scaffold. For instance, a central portion and test arm portions can include the same bioink and be printed at the same time, or at different times, from the same nozzle or different nozzles of the same printer, or from different printers. In some embodiments, different portions of the test bed/scaffolds can printed with a different bioink, or the same bioink but with different added components (test compounds, growth factors, cells, etc.), and be printed from the same nozzle of the same printer at different times, from different nozzles of the same printer (at the same time or different times), or from different printers. The steps can be repeated until all sections/portions of the bioscaffold/ test bed is printed. After printing, the 3D bioprinted test bed is exposed to an initiator/initiator stimulus (e.g., UV light) to complete crosslinking of the MeHA and the ECM components to form the scaffold.

In embodiments, the bioink for the methods of the present disclosure can be any of the bioink compositions described above. For instance, in embodiments, the base bioink composition includes a multi-component methacrylated hyaluronic acid (MeHA)-based hydrogel precursor composition having a MeHA component, an extracellular matrix (ECM) component, and an initiator/crosslinker compotation capable of crosslinking the MeHA component and the ECM component. As discussed above, in embodiments, the MeHA component can include GMHA, MAHA, or a combination thereof, having a concentration of 10-40 mg/mL (e.g., MAHA 10). The ECM component can be, but is not limited to: collagen, laminin, or a combination thereof. In embodiments, the ECM is collagen (such as, but not limited to, collagen I) and has a concentration of about 0.1-50 mg/mL (e.g., about 1-5 mg/mL). In embodiments, the cross-linker/initiator is a photoinitiator compound, such as, but not limited to Irgacure 2959 and lithium phenyl-2,4,6-trimethylbenzoylphosphinate (LAP). As discussed previously, in embodiments, the bioink can be partially cured/gelled prior to printing to improve print quality and then fully cured/ crosslinked after printing by use of an initiator (e.g., a compound, UV light, etc.).

Methods of Comparatively Testing Two or More Test Compounds/Stimuli

Methods of the present disclosure also include in vitro testing two or more compounds or other test stimuli on cells using the 3D bioprinted test beds of the present disclosure. For illustration, embodiments of such methods are described with reference to neuronal cells, but a skilled artisan will understand that the principles and approaches can be applied to other cell/tissue types (e.g., muscle, skeletal, epithelial, fat, stem cells, cancer/tumor cells, etc.). In embodiments, methods of comparatively testing the effect of two or more test compounds/stimuli on neuronal cell behavior include providing a 3D bioprinted test bed of the present disclosure, where the cells in the central portion are neuronal cells. Each arm of the test bed can include a different test compound/stimulus. For instance, in a two-arm test bed, the cells can be printed in the central portion, the first arm can include a first test compound, and the second arm can include a second test compound. It will be understood that the test compounds can be printed in the base hydrogel material of the arm portions or they can be added later. Due to the 3D arrangement of the test beds, in embodiments, the arm portions a printed with the test compounds (e.g., drugs, other bioactive agents, support cells, or other chemical stimuli, or printable physical stimuli, such as density gradients, and the like) within the hydrogel matrix material of the test bed. As described above, the test bed has at least two arm portions but may have additional arm portions for testing additional test compounds/stimuli simultaneously and/or for negative controls (with no test compound/stimuli).

In embodiments, after providing the 3D test bed with the desired structure and test parameters, the 3D test bed is cultured (e.g., in culture medium, in an incubator, in humidified environment, combinations of these conditions, and the like). After culturing, the test bed is analyzed, and the cells are observed to determine various growth/proliferation indicators with respect to the direction of each test arm. For instance, this could include comparing cell growth behavior such as cell growth, cell proliferation, cell migration (distance and direction), and neurite extension (quantity, length, direction, etc. for neural cells). Other possible indicators of cell behaviors that can be analyzed include protein/gene expression, presence/quantity of certain secreted protein products, and measurement of cellular electrical activity.

Additional details regarding the methods, compositions, and organisms of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1-3D Bioprinted Hyaluronic Acid Hydrogel Test Beds for Assessing Neural Cell Responses to Competitive Growth Stimuli Introduction Peripheral nerve injury is a frequent occurrence affecting a considerable percentage of trauma patients with an estimated 500,000 nerve repair and nerve protection procedures performed annually.[1,2] Although the peripheral nervous system has an inherent ability to heal, regeneration only occurs over small gaps and under ideal conditions.[3] Current interventions are unable to bridge large nerve injury gaps (greater than ~7 mm), nor can these methods restore both motor and sensory function to the same degree as the original uninjured nerve.[4] In developing treatments for peripheral nerve injury, there is considerable need for improved in vitro assays and test beds[5] to investigate nerve regenerative factors that mimic the microenvironment of native tissue and improve nerve tissue-engineering scaffolds.

Although in vivo studies are necessary for testing the development of biomedical-engineered devices and pharmaceuticals, there are many limitations with the use of animal models, including ethical considerations,[6] high costs, and questions about the translatability from animal models to humans.[7] This can be a costly and unfortunate problem when developing mechanistic understandings of injury progression and screening for therapeutic modalities. Therefore, there is great interest in the development of advanced in vitro models to reduce reliance on animal research; in vitro systems can also offer potential advantages over the use of animal models (e.g., customization). Such advanced in vitro models should reflect the dynamic physiological changes in neural injuries while addressing the needs of availability and reproducibility better than animal models.[5,8] Not only do they reduce ethical and cost concerns, they also have the potential for patient-specific customization. This will likely involve the continued development of induced pluripotent stem cells,[9] but a robust in vitro model has the potential to use a patient's own cells to test competitive and specific treatment options on an individual basis.

Despite the increase in the use of these advanced in vitro models in general, there is a lack of suitable in vitro peripheral nerve test beds in the field of nerve tissue engineering.[5] The most commonly used in vitro tests include standard 2D cell culture with relevant cell types[10,11] (e.g., Schwann cells, various neural cell lines such as PC-12 cells) or culture of neonatal dorsal root ganglia (DRG) explants in hydrogels.[12,13] Therefore, there is a need to develop peripheral nerve test beds to ease the transition from bench research to in vivo applications. 3D bioprinting allows the customizability of an in vitro system to match complex tissue architectures[14] while also permitting incorporation of various cell types, including patient-derived cells.[15,16]

The development of 3D printing technology for use in tissue engineering has resulted in the fabrication of printed cell-laden scaffold structures that can incorporate cells and growth factors relevant to the tissue. Biomaterial selection is a critical design aspect for bioprinting. To print high-resolution structures, materials used in 3D bioprinting must be capable of deposition on a surface and must maintain a printed structure prior to crosslinking and "locking" the printed shape in place. This depends on the physical, chemical, and rheological properties of the bioinks.[17] In addition, bioinks containing living cells must consider the shear forces applied to cells during printing, especially using an extrusion-based printer. As bioink materials, many different polymeric hydrogel solutions have been adapted for 3D bioprinting because they provide a hydrated 3D network that mimics the microenvironment of native tissue.[17]

Natural biomaterials such as hyaluronic acid (HA) are of interest because of their native physiological roles. HA is an extracellular matrix that plays a major role in wound healing and presents several advantages in tissue engineering: hydrophilicity, non-immunogenicity, biodegradability, biocompatibility, and ease to chemically produce and modify. In addition, HA is already FDA approved for other medical applications.[18] HA can be modified to make polymeric hydrogels, which has potential as a good candidate for the development of a bioink-material used in 3D bioprinting.[19] Some groups have developed modified HA for 3D bioprinting including addition of adamantane or β-cyclodextrin to form a self-healing printed hydrogel,[20] mixtures of methacrylated HA (MeHA) and methacrylated gelatin for bioprinted heart valve conduits,[21] and mixtures of thermogelling HA-poly(N-isopropylacrylamide) with methacrylated HA for increased printability.[22] Although these studies have been critical in developing various methods for bioprinting of HA, none have utilized this printed HA for use in assessing neural cell responses in vitro.

This example establishes 1) the utilization of ECM-based materials (particularly MeHA and collagen-1) as bioink candidates, 2) optimization of methacrylated HA bioinks for neural tissue engineering applications, and 3) the customization of a competitive test bed platform capable of assessing biochemical, physiological, and/or biophysical cues in a 3D context. Combining the tunability of HA and the customizability of 3D bioprinting, this study establishes feasibility to adapt methacrylated HA bioinks to create competitive test bed platforms that can be easily expanded to study nerve repair responses in a 3D context Materials and Methods Chemicals and Materials. All materials obtained from Sigma Aldrich (St. Louis, MO) unless noted otherwise. High molecular weight sodium hyaluronate from *Streptococcus equi* ($1.6 \times 10^6$ Da; 53747), glycidyl methacrylate (779342), triethylamine (T0886), Acetone (A18-20), phosphate buffered saline (P5493-1L), methacrylic anhydride (ThermoFisher Scientific NC9474459; Pittsburgh, PA), 5M sodium hydroxide (221465), and ethanol were used for MeHA synthesis. Photoinitiators used in this study were Irgacure 2959 (I2959; Ciba Specialty Chemicals 55047962; Basel, Switzerland) and lithium phenyl-2,4,6-trimethylbenzoyl-phosphinate (LAP; 900889). Rat tail Collagen I at high concentration (Col-1; Corning 354249; Corning, NY), glacial acetic acid (ThermoFisher BP2401), DMEM 10X (D2429), HEPES buffer (ThermoFisher SH3085101), and sodium bicarbonate (JT Baker 3509-01) were used for the addition of Col-d into MeHA hydrogels. Rat beta-nerve growth factor (NGF; R&D Systems 556-NG-100) and glial cell line-derived neurotrophic factor (GDNF; R&D Systems 512-GF-010/CF) were also used in hydrogel preparation.

Rheological Characterization of HA Hydrogels. After synthesizing two types of HA polymer using the two methods of methacrylation, each type of HA was dissolved in 70% (by volume) deionized water and 30% I2959 to make pre-gel solutions in varied concentrations. MAHA was dissolved at 5, 10, 15, and 20 mg/mL; GMHA was dissolved at 5, 10, 15, 20, and 40 mg/mL. Different hydrogel formulations are denoted as the HA chemistry followed by a number representing the concentration in mg/mL (e.g., GMHA 20 is GMHA dissolved at a concentration of 20 mg/mL). An 8 mm diameter top plate was used in the Anton Paar MCR-302 (Anton Paar, Graz, Austria). The top plate was lowered to a height of 1 mm, and each candidate bioink solution was pipetted into the gap, with an approximate volume of 80 μL of each HA pre-gel solution. Rheological tests were performed under a shear rate ramp from 0.01 to 100 Hz, then under a temperature ramp from 4 to 60° C. Similarly, rheological analysis of HA pre-gel solutions with PC-12 cells at $10^6$ cells/mL was also performed under shear rate ramp from 0.01 to 100 Hz for GMHA 10 and MAHA 10.

Printability of Methacrylated HA Bioinks. Using viscosity values from rheological characterization, a subset of higher viscosity HA solutions were prepared using the previously described protocol. MAHA was dissolved at 10 mg/mL (either with or without 3 mg/mL of pH-neutralized Col-I) and 20 mg/mL. GMHA was dissolved at 10,20 (with and without 3 mg/mL of pH-neutralized Col-I), and 40 mg/mL. The design consists of 2 layers printing perpendicular to each other. After each print, an image of the printed grid was taken with a camera attached to a Zeiss Stemi 2000-CS light microscope. Using ImageJ, the color threshold was adjusted to isolate the printed grid from the image background.

ImageJ was used to measure the area and perimeter of the squares in the grid to calculate circularity (C) and Printability (Pr). Circularity describes how circular a shape is with a perfect circle having a value of 1; the following formula is commonly used for shape factor image analysis:

$$C = \frac{4\pi A}{L^2} \qquad (1)$$

Pr is a function of circularity used for bioink evaluation.[26] It is based on squares instead of circles and is defined in the following equation. The percentage of printed squares (out of an expected total of 25) was also recorded for each HA sample print. For a perfectly printable bioink, the connected filaments would form perfect squares and Pr=1. Larger printability values correspond to squares and more gelation of the bioink, whereas smaller printability values correspond to circles and less gelation of the bioink. The fraction of printed squares was multiplied by Pr to give an Adjusted Printability (AP) score to account for the number of printed squares in the score.[26]

$$Pr = \frac{\pi}{4} * \frac{1}{C} \quad (2)$$

$$\% \text{ Printed} = \frac{\text{squares printed}}{25} * 100 \quad (3)$$

$$AP = Pr * \% \text{ Printed} \quad (4)$$

Printing Parameters for in vitro Testing. Unless noted otherwise, the bioink selected for later experiments was MAHA at a concentration of 10 mg/mL mixed with 3 mg/mL of pH-neutralized Col-d, 3 mg/mL of specified photoinitiator (either LAP or I2959) dissolved in deionized water. A 27-gauge needle with a print speed of 10 mm/s, layer height of 0.337 mm, and pressure between 50-70 kPa was used for extrusion. The UV time was set to 2 seconds following every 2 layers being printed on the Cellink Bio X.

Schwann Cell (SC) Adhesion to Bioink Materials. MAHA 10 only, Col-d only, and MAHA 10/Col-I were used to coat the surface of a 24 well-plate. Rat SCs were seeded at a density of 8,000 cells per well and cultured for 5 days before fixing and staining with anti-integrin 31 (n=4) to assess cell adhesion. Fluorescence images (n=2 per sample) were acquired using a Zeiss Axio Observer microscope at magnification of 10×. ImageJ was used to threshold positive integrin 31 signal for all images. Mean intensity, area per cell and total positive area were measured as indicators of SC adhesion. Mean intensity, positive area, and percent area were normalized to the positive control, Col-d, for direct comparison.

SC Migration in 3D Bioprinted Hydrogels. The experimental groups included 1 μg/mL of NGF or GDNF encapsulated within 1 mL of bioink, whereas the control group contained no growth factor (no GF) (n=5). The bioinks were used to print a cylinder of 8 mm diameter and 2 mm height. The control group was printed without any growth factor. Next, SCs were seeded on top of the hydrogels at a cell density of $10^5$ cells/cm$^2$ and cultured for 7 days with the media changed every 2 days. Hydrogel samples, stained using a Live/Dead assay, were then placed cell-side-down in a 35-mm diameter glass-bottom dish and imaged using a Zeiss LSM 880 laser-scanning confocal microscope. Z-stacked image of 500 μm deep at 10× magnification were analyzed to assess SC migration into the hydrogel using a Zeiss ZEN 2 software by creating a heat map based on relative depth within the hydrogel to measure the farthest migration points (n=5) in each sample. By taking the average of cell migration depth, this assessment examined the total migration into the biomaterials in 3D culture.

DRG Neurite Outgrowth in Competitive in vitro Test Beds. A 6-layer rectangular model with two arms or "chambers" were printed on each end (12 mm long, 5 mm wide, and 1.7 mm height). A base layer (0.7 mm height) was printed containing only the hydrogel. On top of the base on either side two "chambers" were printed; each chamber contained a concentration of 1 μg/mL of either NGF, GDNF, or no GF as control. To establish a competitive cue assay, three test bed groups were printed: NGF versus control (NGF/control), GDNF/control, or NGF/GDNF. To identify test bed orientation, one chamber had squared ends and the other had rounded ends as shown in FIG. 1. DRGs were trimmed on the same day as testbed fabrication. Each DRG was semi-encapsulated at the center of the hydrogel testbeds by first placing the DRG directly in the middle of the two-chambered testbed and then securing in place with pH-neutralized Col-d solution at a concentration of 3 mg/mL. Col-d allowed for securing the DRG quickly without the need for direct UV exposure of the DRG. The test beds were incubated for 30 minutes to allow for collagen gelation and then media was added. Media was changed three hours following the addition of DRGs to account for bulk growth factor release into the media. DRGs were cultured for 7 days with media being changed every 2 days.

Following 7 days of culture, DRGs were fixed in 2% paraformaldehyde for 1 hour followed by three PBS rinses of 45 minutes each before blocking in 0.3% Triton X-100 and 3% goat serum in 1×PBS for 1 hour. The primary antibodies used were β-III tubulin to identify microtubules (i.e., indicating neurite extension) and GAP43, a "plasticity" protein that is expressed at high levels in neuronal growth cones (a secondary indicator of new neurite formation). Both antibodies were diluted at 1:500 dilutions and incubated on samples at 4° C. for 48 hours. DRGs were then washed with 0.05% Tween-20 in 1×PBS three times for 6 hours each. Secondary antibodies, AlexaFluor 488 α-rabbit and AlexaFluor 568 α-mouse at 1:500 dilutions, were added for 16 hours in blocking buffer. DRGs were rinsed with 0.05% Tween-20 in 1×PBS three times for 6 hours each. Cell nuclei were stained with DAPI in deionized water for 5 minutes at room temperature. For β-III tubulin marker, top-view images of DRGs were acquired with a Zeiss Axio Imager 2 microscope. ImageJ and the neurite tracer plugin were used to quantify neurite lengths extending from the DRG body. From a ranked list of directional neurite lengths, the five longest neurite extensions were averaged for each chamber side. These results were then averaged for DRGs cultured in each hydrogel type. For the GAP43 marker, samples were imaged from the top with a Zeiss LMA 880 confocal microscope. ImageJ was used to threshold positive signal for all images. Positive area was measured as directional outgrowth from each DRG in the left and right directions toward the growth factor chambers relative to the center of the DRG body. The positive area of each side was normalized to the total positive signal of the whole image.

Statistics Analysis. GraphPad Prism 6 (GraphPad Software Inc., San Diego, CA) was used for statistical analysis. ANOVA and unpaired t-test with Welch's correction were used to compare results among the different hydrogels depending on the experiment. Significance was considered for $p<0.05$. Results are displayed as ±standard deviation.

Results

As mentioned above, different hydrogel formulations are denoted as the HA chemistry followed by a number representing the concentration in mg/mL (e.g., GMHA 20 is GMHA dissolved at a concentration of 20 mg/mL).

Rheological Properties of MeHA Solutions without the Presence of PC-12 Cells. Several bioink candidates were rheologically characterized, including GMHA at concentrations of 5, 10, 15, 20, and 40 mg/mL and MAHA at 5, 10, 15, and 20 mg/mL. After the shear rate sweep with varying shear rate from 0.1 to 100 Hz, rheological analysis showed that HA pre-gel solutions exhibited shear thinning properties in which viscosity decreased under increased shear strain, FIG. 2A. At lower concentrations, for example, GMHA 5 had a viscosity of 0.15±0.04 Pa·s at 0.1 Hz that dropped to 0.030±0.002 Pa·s at the highest shear rate of 100 Hz. Likewise, MAHA 5 had a viscosity of 0.14±0.07 Pa·s at 0.1 Hz that dropped to 0.037±0.001 Pa·s at the highest shear rate of 100 Hz. In all cases, increasing the concentration of MeHA resulted in higher viscosities, as expected. However, MAHA at the same concentration as GMHA typically had a higher viscosity. For example, GMHA 40 had a viscosity of 24.5±1.2 Pa·s at the shear rate of 0.1 Hz and 3.9±0.8 Pa·s at the highest shear rate of 100 Hz whereas MAHA 20 at 0.1 Hz had a viscosity of 30.5±9.2 Pa·s that dropped to 1.1±0.2 Pa·s at the highest shear rate of 100 Hz. Although all rheological data showed shear thinning properties for MeHA, the range of viscosities varied considerably depending on the concentration, and MAHA was more viscous relative to GMHA at a given concentration.

In the temperature sweeps, the same trend continued with higher concentrations resulting in higher viscosities. Higher temperatures resulted in lower viscosities in all tested bioink candidates. By varying the temperature (4 to 60° C. is the temperature range of the Cellink Bio X printer), viscosity can range from 0.08 to 8.73 Pa·s, respectively, as shown in FIG. 2B. These results indicate that varying the printing temperature is a potential tool to achieve optimal print quality with these candidate MeHA bioinks.

Rheological Properties of MeHA Solutions with the Presence of PC-12 Cells. Shear rate sweeps were conducted on GMHA 10 and MAHA 10 both with and without PC-12 cells. Based on the results shown in FIG. 2C, the addition of PC-12 cells at $10^6$ cell/mL did not result in a significant difference in viscosity, indicating that HA pre-gel solutions with cells can meet the viscosity requirements of a suitable bioink.

Figure 3A:
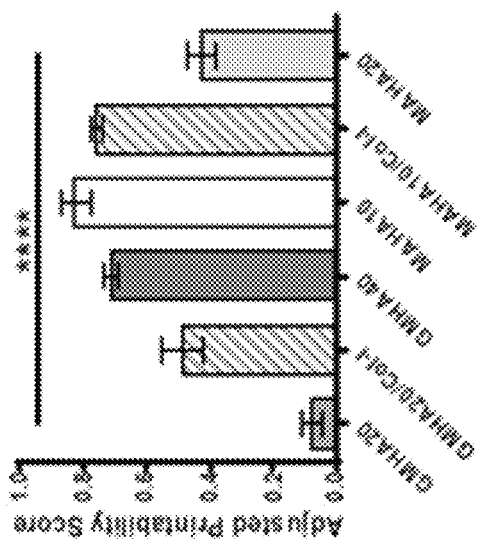
Figure 3B:
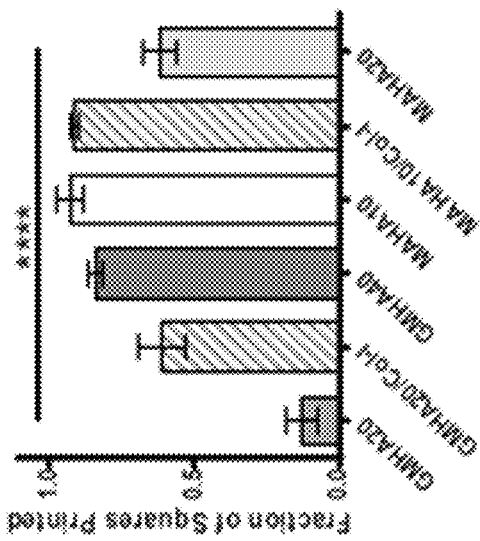
Figure 3C:
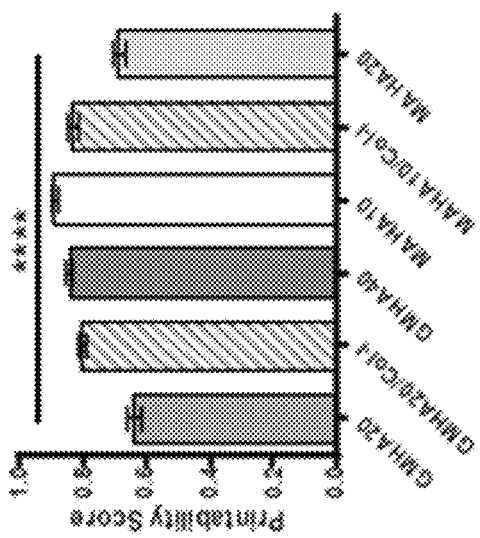
FIG. 3C illustrates rheological characterization of bioink candidates both with and without cells (in the graph MAHA 10 with and without cells is the upper set of data points). Viscosity was characterized as a function of shear rate of MAHA 10 and GMHA 10 with and without cells. Note: Because rheological data is displayed in logarithmic axis, error bars are only showed in one direction for all measurements. For data points without error bars, the SDs are smaller than the size of the data icon.
Figure 3D:
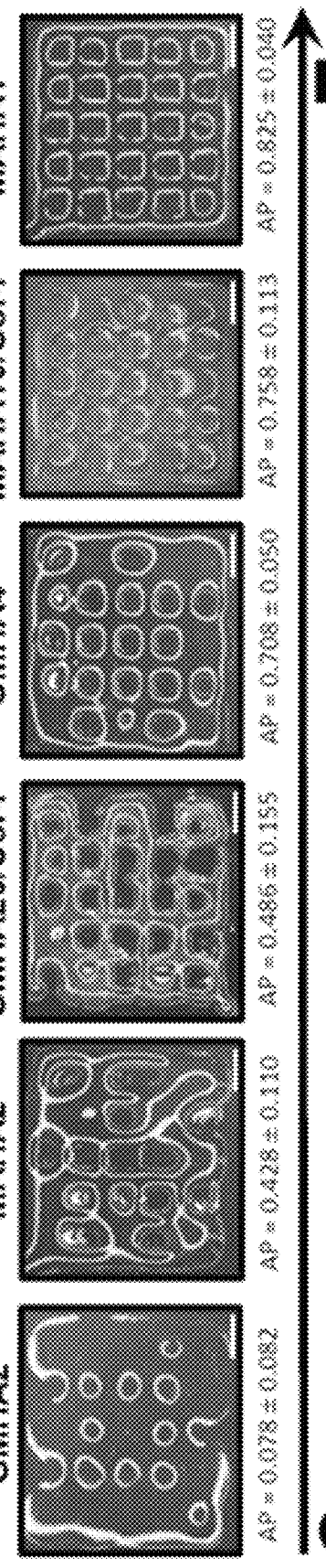

Printability of MeHA Bioinks. As described in the Materials and Methods section above, printability scores were evaluated using image analysis of printed grid patterns. A score of 1.0 is considered a "perfect" print. These methods are derived from a study by Ouyang, et al.[26] Across the six candidate bioinks, the printability scores ranged from 0.64±0.05 for GMHA 20 at the lowest to 0.89±0.03 for MAHA 10 at the highest, as shown in FIG. 3A. However, to account for the fact that not every square was printed within each grid (FIG. 3B), adjusted printability scores are shown in FIG. 3C and listed in ascending order of AP scores in FIG. 3D. The adjusted printability scores of GMHA 40, MAHA 10, and MAHA 10/Col-I were significantly greater than the other candidate bioinks as shown in FIGS. 3C-3D. Based on the early results of the rheological characterization, GMHA 5, GMHA 10, GMHA 15 and MAHA 5 were eliminated as potential bioink candidates because of low viscosity, which can be difficult to print with high fidelity using an extrusion-based 3D bioprinter. The decision to move forward with MAHA10/Col-I for this example was based on the high printability and because the addition of Col-d in the bioink can improve partial gelation when printing and cell adhesion when culturing.

Figures 4A, 4B, 4C:
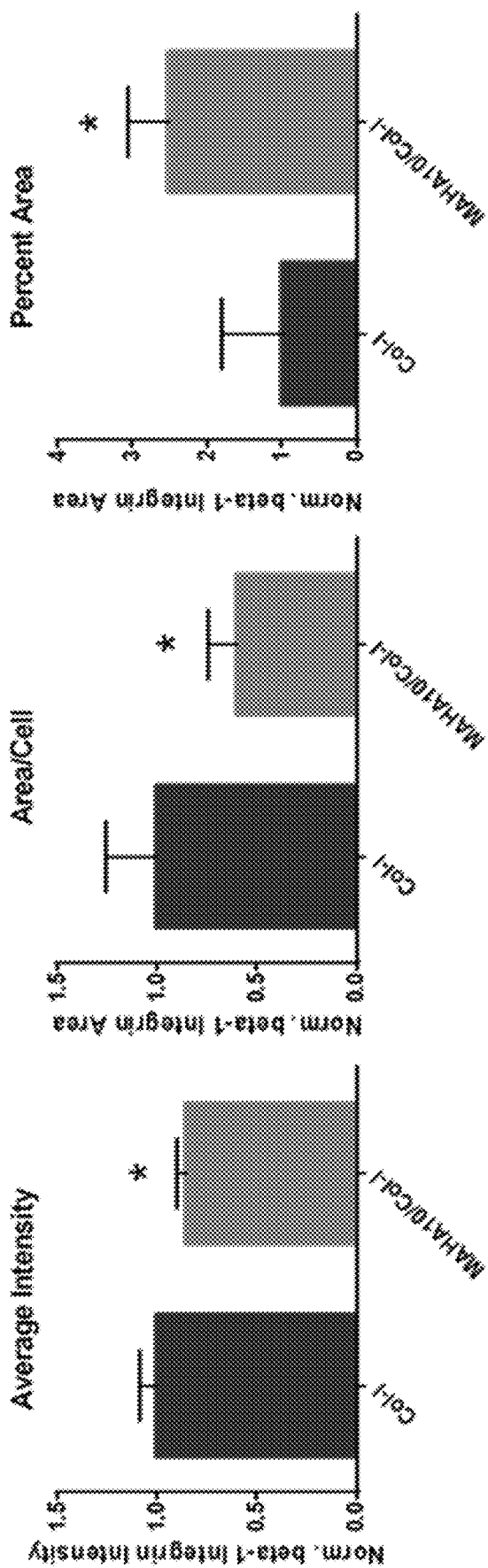
FIGS. 4A-4C illustrate normalized integrin β1 positive expression of Schwann cells (SCs) after 5 days in biomaterials: MAHA 10/Col-I and Col-d as positive control.

SC Adhesion to Bioink Materials. Because Col-d is highly cell-adhesive and serves as a ligand for multiple integrin 31-associated receptors,[27] Col-I only hydrogels were used as a positive control to determine the bioink candidate's (MAHA 10/Col-1) influence on SC adhesion and migratory potential using integrin β1 immunostaining. Although significantly less than Col-d, the average intensity for integrin β1 signal indicated 85.4±3.6 percent for cells grown in MAHA 10/Col-I compared to purely adhesive Col-d gels (FIG. 4A). Moreover, the percent area (i.e., total coverage) of integrin β1 staining was significantly higher for the MAHA 10/Col-I bioink candidate in comparison to Col-d only despite less area per cell (FIGS. 4B and 4C). Meanwhile, MAHA 10 alone did not support SC adhesion at all (no detectable signal). Together, these results indicate that MAHA 10/Col-I as the bioink candidate supports appreciable SC adhesion compared to Col-d and even encourages attachment of a higher number of integrin 31-expressing cells after 5 days.

Figure 5:
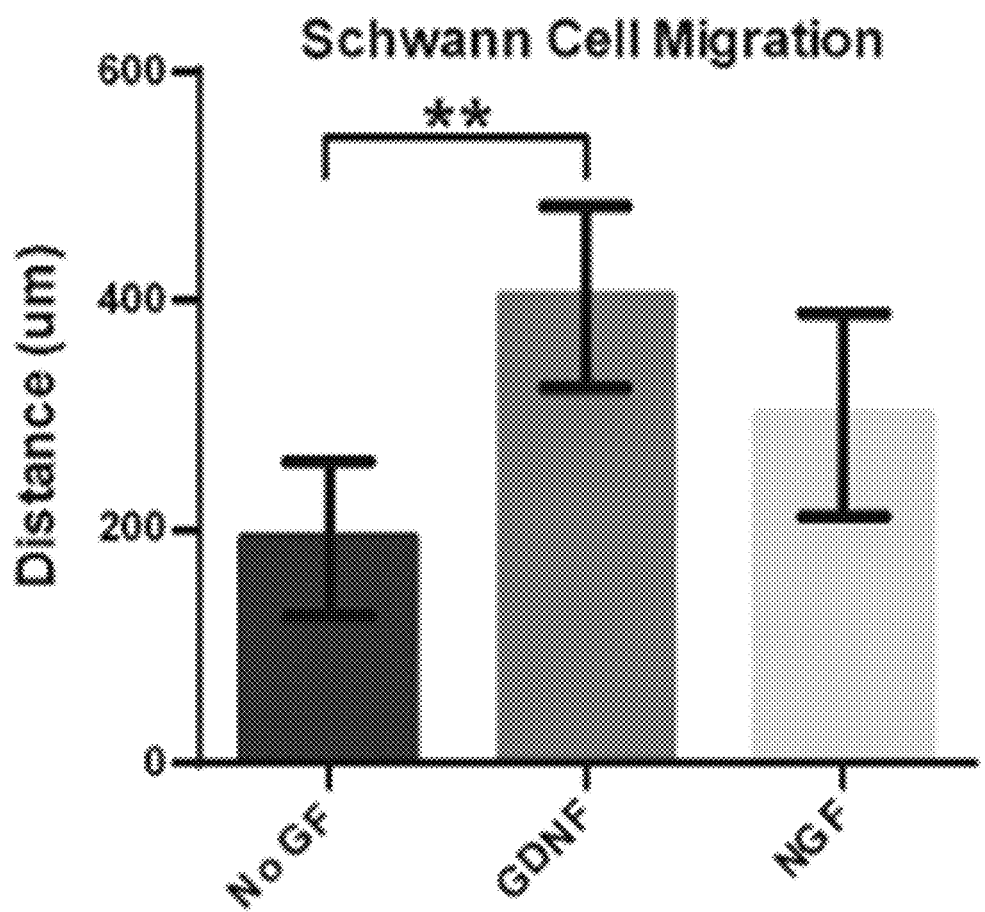
FIG. 5 illustrates a Schwann cell migration assay into bioprinted hydrogels containing no GF, GDNF or NGF after 7 days in culture (n=5). Schwann cells tended to migrate farther in scaffolds bioprinted with GDNF. **p≤0.01.

SC Migration in 3D Bioprinted Hydrogels. A SC migration assay was conducted on bioprinted hydrogels. The bioprinted control group contained no GF, whereas the experimental group either contained NGF or GDNF. After 7 days seeded and cultured on the hydrogels, SCs migrated distance into hydrogels with NGF, GDNF, or no GF were measured respectively as 301±89.4 µm, 403±79.6 µm and 192±66.8 µm. Although SCs seeded on bioprinted hydrogels with NGF migrated slightly farther than the control, there was no statistical difference found. Meanwhile, the bioprinted hydrogels with GDNF has the furthest Schwann cell migration into the hydrogels than the controls with a significant difference as shown in FIG. 5.

DRG Neurite Outgrowth in Competitive in vitro Test Beds. Three different DRG test beds printed were NGF/control, GDNF/control, and NGF/GDNF. As the DRGs were placed in the center of the bioprinted test beds, DRG neurites (as captured in a top view) were quantified based on directional growth from the DRG body towards either chamber containing NGF, GDNF, or no GF using two neuronal growth markers: β-III tubulin (FIG. 6F) and GAP43 (FIG. 6I). For β-III tubulin, average neurite length in either direction is quantified and shown in FIG. 6F. In the NGF/control test beds, the ratio of neurite length on the NGF side to control side was 1.42±0.13 (with significantly greater length towards the NGF-containing chamber relative to control). In the GDNF/control test beds, the ratio of neurite lengths of GDNF side to control side 1.41±0.06 for GDNF/control (significantly greater length towards the GDNF-containing chamber relative to control). However, when comparing NGF and GDNF, the ratio of NGF to GDNF was 1.09±0.19 for NGF/GDNF, and directional neurite length was not significantly different. Therefore, both NGF and GDNF elicited directional neurite outgrowth and competed similarly with one another.

After thresholding GAP43 images on ImageJ, the positive area, indicating positive signal, was normalized to total positive area of the images for each side of the DRG in the test beds (FIG. 6I). In the NGF/control test beds, the fraction positive signal of NGF was 0.63 versus the control of 0.37 (±0.14), indicating a trend toward directional growth but with no significant difference given the low sample size. In the GDNF/control test beds, the fractional positive signal of GDNF side was 0.66 versus the control of 0.34 (±0.12) with significant differences. However, when comparing NGF and GDNF (0.58 versus 0.42, respectively; ±0.12), there was no significant difference in neurite growth in either direction.

Discussion

Three-dimensional bioprinting is an additive manufacturing process in which biomaterials such as hydrogels are combined with cells and growth factors, then printed to create complex structures that imitate natural tissues.[28] To produce complex structures, the bioink to be used for 3D bioprinting must adequately solidify to retain the desired shape upon leaving the print nozzle. Therefore, a suitable bioink material must be able to transition from fluid to gel phase within a specific timeframe. Important factors to consider for bioink materials are rheological properties and crosslinking methods.[29]

As discussed above, HA is a widely used material in tissue engineering and is a suitable material for the development of peripheral nerve in vitro test beds. HA is found in a wide variety of tissues, is highly modifiable, and plays a known role in various regenerative processes, including in the nervous system.[24] This makes HA an attractive material for use as a bioink. However, there are certain considerations for deciding what bioink to use with extrusion-based bioprinters, such as the Cellink Bio X printer that was used for these studies. A bioink for use with extrusion-based bioprinters must meet certain requirements including high viscosity with shear thinning properties. Shear thinning allows the bioinks to be easily extruded while the high viscosity helps the material hold its shape until crosslinked. Shear thinning also has a protective effect on cells printed with extrusion-based bioprinters. Quick crosslinking is desirable so that the shape of the print can be "locked" into place before the printed bioink loses its shape.

Considering all the benefits of HA, MeHA was considered for use in bioprinting. There are several challenges using MeHA that must be overcome for its use in bioprinting applications. While the pre-hydrogel solution viscosity can vary greatly, the higher viscosity solutions can be difficult to dissolve. In addition, UV crosslinkable methacrylated biomaterials such as the MeHA used in this study can have their crosslinking properties modified by the choice of photoinitiator. In addition, modifications to the bioink composition can help create a suitable bioink while still utilizing MeHA as the base bioink material.

After examining the rheological properties of MeHA-based pre-gel solution, the results indicate that MeHA solutions are a viscoelastic fluid and exhibit shear thinning properties. The viscosity of pre-gel solutions can be modified by varying the concentration of MeHA. By increasing the concentration, the viscosity also increases. The viscosity of MeHA pre-gel solutions is also dependent on temperature, in which viscosity decreases when temperature rises. Lastly, MeHA is photocrosslinkable. By adding the photoinitiator, MeHA transforms from the fluid to gel phase under UV light. Post-fabrication crosslinking of MeHA bioinks helps promote mechanical stability of printed objects.[30] With I2959, the crosslinking can still take minutes, rather than the seconds as desirable. However, there are other potential photoinitiators, such as LAP, which may eliminate some of the issues with I2959.[31]

Other groups have developed various other HA chemistries as bioinks. Ouyang, et al. developed a MeHA bioink coupled with either adamantane or β-cyclodextrin moieties that formed two hydrogel precursor solutions that assemble when mixed.[32] Kesti, et al. developed a MeHA and HA-poly(N-isopropylacrylamide) copolymer for bioprinting applications,[22] in which the copolymer provides fast thermal gelation, whereas the MeHA allows for long-term stability. Kiyotake, et al. developed a pentenoate-functionalized HA for use as a bioink.[33] Poldervaart, et al. have reported on basic bioprinting with MAHA-based hydrogels.[34] They fabricated MAHA hydrogels with low degrees of methacrylation ranging between 5-7% (as opposed to the 30% used here) and concentrations ranging from 10 to 30 mg/mL. They found that mesenchymal stromal cells were able to survive with high viability following bioprinting within their MAHA hydrogels.

Material printability depends primarily on the viscosity of the bioink and can therefore be modulated by changing parameters that control the viscosity such as temperature or shear (which can be indirectly controlled by changing print parameters such as nozzle diameter and print pressure). The addition of Col-d to the HA hydrogels solution during printing can be used to tune the viscosity, hold the shape of printed structures prior to crosslinking, allow for cellular adhesion, and protect cells under the high shear conditions of printing. Because the viscosity of Col-I can be adjusted through concentration and temperature, it is a good additive for the improvement of printability (in addition to its biological benefits). Determining the window of suitable bioprinting parameters is critical as this determines whether a material can be suitably used as a bioink. Composite hydrogel solutions of MeHA with Col-d were found to be printable up to 2 hours following solution mixing.

Based on the image analysis used to quantify bioink printability, a suitable bioink candidate was selected based on consistent grid patterns and shape of void spaces. A printability score of 1 indicates a "perfect" square. To account for the inconsistency in whether full grids were capable of being printed (for example, see GMHA 20 and MAHA 20 in FIG. 3D), the printability score was adjusted to account for the percentage of squares printed out of the expected 25 squares within the grid. From this adjusted printability scores, MAHA 10 had the highest printability scores and consistent number of squares printed with the adjusted printability score of 0.825 (FIGS. 3C, 3D). In comparison to MAHA 10, MAHA 20 had a lower printability score despite the higher concentration. One possible explanation is that the 2-layer grid printability assay was assessed at a constant print speed, pressure, and nozzle size for all hydrogel solutions. MAHA 20 might require further optimization of printing pressure and nozzle size to improve printability. Furthermore, as MAHA at the same concentration as GMHA typically had a higher viscosity as shown with rheological measurements, it was not possible to dissolve MAHA at concentrations higher than 20 mg/mL to make MAHA 20/Col-I hydrogel solution for this assay. The addition of Col-d slightly lowered the adjusted printability score of MAHA 10. However, because HA is non-adhesive, Col-d helps to provide cell adhesion for the purpose of bioprinting and incorporating cells in later applications,[35] which outweighed the minor drop in print fidelity. Therefore, the bioink selected for use in the in vitro portions of this study was a mixture composed of MAHA at 10 mg/mL and Col-d at 3 mg/mL to increase cell adhesion. To improve the developed HA-collagen bioink, it would be advantageous to further investigate different ratios of MAHA to Col-d to optimize viscoelastic properties of the bioink flow in the viscous/liquid phase. Although the addition of Col-d aided with the biological properties of the material, it complicated the printing process. For example, a high concentration of collagen within the bioink formulation was found to gel at a quicker rate, clogging the printing nozzle.[36] Therefore, an optimized formulation of MAHA and Col-d can aid the bioink in maintaining its shape prior to crosslinking, improving the printability.

To determine the functionality of this bioink for peripheral nerve applications, SC adhesion to the selected MAHA 10/Col-I bioink was examined in comparison to a known adhesive Col-d substrate. After peripheral nerve injury, the signaling interaction of activated SCs with axons is critical for initiating axonal elongation, remyelination, and correct targeting for functional recovery.[37] Because SC migration is a critical component of nerve repair and regeneration, it is important that the bioink candidate adequately support SC adhesion. SC adhesion was analyzed using integrin β1 immunostaining. In this study, MAHA 10/Col-I maintained approximately 85.4 percent of the purely adhesive Col-d positive control. Meanwhile, the percent area coverage of positive integrin β1 expression was significantly higher for MAHA 10/Col-I indicating a higher number of cells expressing integrin β1 expression interacting with the candidate bioink. The results therefore demonstrate that modification of Col-d, which does not have ideal bioprinting properties, to include MAHA-10 does not appreciably hinder SCs adhesion via integrin β1. Integrin β1 in SCs has been reported to play a role in integrating signals with the basal lamina component and mediating the radial sorting of axons at the early steps of myelination in developing neurons.[38,39] Aligned with previous studies[35], to compensate for the non-adhesivity of HA, the addition of other adhesive ECM component is included to enhance bioink optimization and improve the cell functionality printed in gels.

Continuing with bioink optimization, a supplemental rat fibroblast viability study showed a significant increase following printing in the bioink and depending on the photoinitiator used. The study indicated that printing actually increased viability by 20% compared the molded controls. Results of this study indicated that LAP indeed supported the highest viability of bioprinted cells as compared to I2959 counterparts, with a significant difference compared to molded samples crosslinked with I2959. It is anticipated that crosslinking time can be reduced for the LAP group in the future to further increase viability.[40] Therefore, LAP became the crosslinker used for the later experiments for the advantages of LAP over I2959, as previously reported.[31,41]

Next, with the goal of designing an in vitro test bed for neural applications, the selected bioink was used to sequester different growth factors to study variable levels of SC migration as illustrated in FIG. 5. Following nerve injury, SCs play a critical role in peripheral nerve regeneration as they migrate into the site of injury, releasing neurotrophic growth factors and forming the bands of Büngner that aid with nerve realignment and remyelination.[42] The SC migration assay involved 3D bioprinted MAHA 10 and Col-d hydrogel encapsulated either with or without growth factor. SCs were seeded on top of the bioprinted scaffold and a Live/Dead stain and confocal imaging was used to assess SC migration following 7 days in culture. We found that SCs tended to migrate farther into the bioprinted hydrogel with GDNF than into the hydrogel with NGF. Previous studies have also shown that NGF and GDNF behave as chemoattractant for a SC precursor line.[43] GDNF was shown to stimulate glial cell motility.[43,44] These results indicate that MeHA/Col-I printed matrices support growth factor sequestration effective at causing differential SC responses via infiltration into the printed materials. Thus, future adaptations of the test beds can be envisioned to examine the contribution of certain chemical molecules to stimulate cellular interaction and regeneration for nerve tissue engineering applications.

Figure 6A:
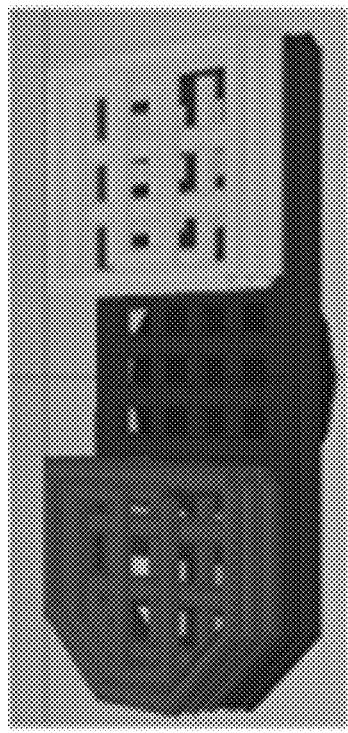
Figure 6B:
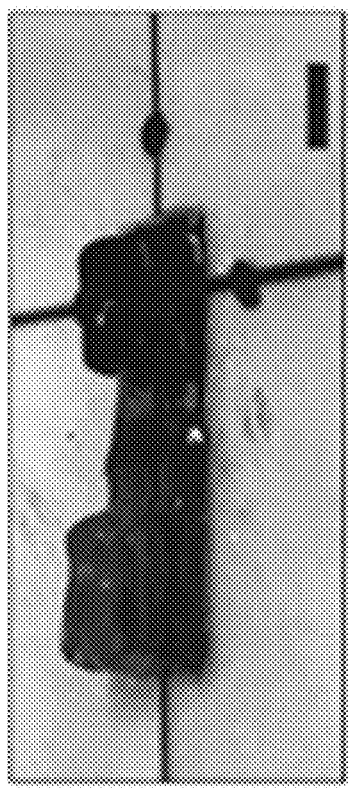
Figure 6C:
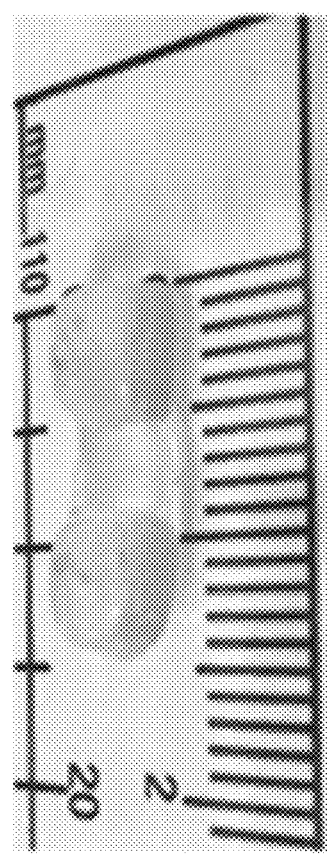

To further showcase the use of ECM-based bioinks and the advantage of 3D bioprinting techniques in neural tissue engineering, a 3D bioprinted DRG neurite extension test bed was designed and used to assess neurite outgrowth. In the DRG neurite extension in vitro test bed, two "chambers" with different growth factors were successfully printed to assess neurite directionality. A schematic of the 3D test bed is illustrated in FIG. 6A, with FIG. 6B showing a 3D printed test bed using MAHA 10 with a different color of food coloring included with the bioink printed from separate nozzles to illustrate the different prints from each nozzle. FIG. 6C illustrates a final 3D bioprinted test bed before DRG seeding.

The test beds allowed direct comparison through directional growth of the DRGs between NGF/GDNF and either growth factor against a control without growth factor. β-III tubulin was used to mark neurite extension because it is a highly expressed cytoskeletal protein found almost exclusively in neural cells. Previous studies have shown an initial decrease in β-III tubulin mRNA levels in axotomized DRG neurons compared to contralateral controls at 1 day after injury followed by a robust increase in β-III tubulin mRNA levels relative to contralateral controls from 1 to 4 weeks after injury.[45] Based on β-III tubulin staining (FIGS. 6D, 6E and 6F), DRG neurites significantly extended towards growth factors relative to the control after 7 days.

NGF was studied as a selective biochemical cue to enhance sensory neurite outgrowth whereas GDNF enhances both motor and sensory neurite outgrowth; however, DRGs are associated primarily with sensory neurons.[46] In the NGF/GDNF test beds, there was no significant statistical difference in either direction; however, the neurites growing toward NGF averaged slightly longer than toward GDNF. Although this result was not significantly different, the trend does correspond with previous studies exploring the functions of different growth factors critical for peripheral nerve regeneration.[46,47] This test bed design can potentially offer a platform to examine different dosing values and mixtures of growth factors to stimulate neurite outgrowth.

The protein GAP43 indicates the presence of neural growth cones and processes associated with neuronal development and regeneration.[3,48] Therefore, expression of GAP43 was used as a secondary indicator for DRG neurite outgrowth in the in vitro test beds for neuronal development and regeneration (FIGS. 6G, 6H and 6I). In the GDNF/control test bed neurites toward the GDNF side expressed significant GAP43 signal relative to the control group, while neurites in the NGF/control test beds did not show significant difference (FIG. 6I). For the NGF/GDNF test bed, no significant difference was found, although NGF trended toward higher GAP43 signal than GDNF side.

Overall, the combined results indicate that 3D bioprinted MeHA/Col-I hydrogels can support incorporated cells and/or growth factor stimuli and therefore have potential to be developed into more comprehensive peripheral nerve in vitro test beds. In nerve tissue engineering, the most common used in vitro tests include standard 2D cell culture with relevant cell types or neonatal DRG. In a previous study in the Schmidt lab, Gomez, et al. described a 2D neuronal competitive assay to compare multiple methods for neurite extension of hippocampal neurons; these neurons were found to show preferential growth towards physical cues relative to chemical cues.[49] Therefore, 3D bioprinting technology can enhance the capability of incorporating microscaled structure along with the addition of chemical cues to improve tissue engineering scaffolds.[50]

Furthermore, 3D bioprinting can also improve the ability to integrate multi-component diffusive biomolecular gradients as shown by the 3D printed bifurcated nerve guide by Johnson, et al. using silicone[51] to mimic complex mixed nerve injuries, but utilizing ECM-derived biomaterials[52,53] instead. The test bed described here does not utilize any controlled release of growth factors. However, based on literature, this is still sufficient to influence DRG behavior. Leach, et al. used a methacrylated HA scaffold that was either unmodified or modified with polyethylene glycol.[54]

The use of polyethylene glycol did slow the release of protein (in this study, bovine serum albumin release was observed), but HA alone was still sufficient to slow the release of these factors to form a gradient effect. In a different study, Santos, et al. observed the dose-dependent effects of various growth factors on DRG and SC neurite extensions.[46] The growth factors were simply loaded into hydrogel scaffolds (in Santos' study, the scaffolds were a Col-d matrix) and neurite extensions quantified following two or four days in culture (for DRGs or SCs, respectively). They found that NGF increased sensory neurite extensions while GDNF increased both sensory and motor neurite extension. This platform could potentially be used to further evaluate these dose-dependent and gradient effects. 3D bioprinting as a technique offers potential advantages for such a study, for example, the dimensions of the growth factor-releasing chambers can be modified to allow for precise control of the resulting growth factor gradients.

Overall, this example described tunable properties of HA for 3D printing bioink material development. The 3D bioprinted test bed design described here shows a customized 3D culture system and a method to analyze neuronal development from 3D cultured system, utilizing explanted DRGs which resemble physiological regeneration better than traditional 2D cell culture systems used in nerve tissue engineering. This in vitro system can potentially be applied beyond testing growth factors or other molecular drug candidates by the inclusion of mechanical or physical growth cues.[49] Further development of this platform could allow for a fully three-dimensional test bed assay to competitively assess a wide variety of cues in peripheral nerve regeneration including chemical drug candidates[56,57], physical cues[12,58], and electrical stimulation[59-61]. This approach can both improve upon current understanding of physiological neural growth as well as to develop future treatments to aid in peripheral nerve regeneration.

CONCLUSIONS

In conclusion, MeHA is a viable bioink for use in extrusion-based bioprinting, particularly when combined with other ECM components such as Col-d. The addition of Col-d to MeHA-based hydrogel solutions helps maintain suitable viscosity for printing, holds the shape of printed structures prior to crosslinking, and improves cell protection and adhesion. With the use of 3D bioprinting, this HA-based material was used as a bioink to create a competitive DRG neurite extension assay that could prove useful for tissue engineers looking for a more advanced, customizable and reproducible in vitro test method or an alternative to common in vivo tests.

REFERENCES (1) Taylor, C. A.; Braza, D.; Rice, J. B.; Dillingham, T. The Incidence of Peripheral Nerve Injury in Extremity Trauma. *Am. J. Phys. Med. Rehabil.* 2008, 87 (5), 381-385. https://doi.org/10.1097/PHM.0b013e31815e6370.
(2) Brattain, K. Analysis the Peripheral Nerve Repair Market in the United States. *Magellan Med. Technol. Consult. Inc.* 2014.
(3) Brushart, T. M. *Nerve Repair*, Oxford University Press, 2011.
(4) Mobini, S.; Spearman, B. S.; Lacko, C. S.; Schmidt, C. E. Recent Advances in Strategies for Peripheral Nerve Tissue Engineering. *Current Opinion in Biomedical Engineering.* Elsevier B. V. Dec. 1, 2017, pp 134-142. https://doi.org/10.1016/j.cobme.2017.10.010.
(5) Mobini, S.; Song, Y. H.; McCrary, M. W.; Schmidt, C. E. Advances in Ex Vivo Models and Lab-on-a-Chip Devices for Neural Tissue Engineering. *Biomaterials* 2019, 198, 146-166. https://doi.org/10.1016/j.biomaterials.2018.05.012.
(6) Ferdowsian, H. R.; Beck, N. Ethical and Scientific Considerations Regarding Animal Testing and Research. 2011, 6 (9). https://doi.org/10.1371/journal.pone.0024059.
(7) Wendler, A.; Wehling, M. The Translatability of Animal Models for Clinical Development: Biomarkers and Disease Models. *Curr. Opin. Pharmacol.* 2010, 10 (5), 601-606. https://doi.org/10.1016/j.coph.2010.05.009.
(8) Sebastianelli, L.; Versace, V.; Nothdurfter, W.; Saltuari, L.; Taylor, A.; Trinka, E.; Nardone, R.; Brigo, F.; Nardone, R.; Trinka, E. Functional Reorganization after Hemispherectomy in Humans and Animal Models: What Can We Learn about the Brain's Resilience to Extensive Unilateral Lesions? *Brain Research Bulletin.* Elsevier Inc. May 1, 2017, pp 156-167. https://doi.org/10.1016/j.brainresbull.2017.04.005.
(9) Wang, A.; Tang, Z.; Park, I. H.; Zhu, Y.; Patel, S.; Daley, G. Q.; Li, S. Induced Pluripotent Stem Cells for Neural Tissue Engineering. *Biomaterials* 2011, 32 (22), 5023-5032. https://doi.org/10.1016/j.biomaterials.2011.03.070.
(10) Chafik, D.; Bear, D.; Bui, P.; Patel, A.; Jones, N. F.; Kim, B. T.; Hung, C. T.; Gupta, R. Optimization of Schwann Cell Adhesion in Response to Shear Stress in an in Vitro Model for Peripheral Nerve Tissue Engineering. *Tissue Eng.* 2003, 9 (2), 233-241. https://doi.org/10.1089/107632703764664701.
(11) Rubenstein, R.; Carp, R. I.; Callahan, S. M. In Vitro Replication of Scrapie Agent in a Neuronal Model: Infection of PC12 Cells. *J. Gen. Virol.* 1984, 65 (12), 2191-2198. https://doi.org/10.1099/0022-1317-65-12-2191.
(12) Pateman, C. J.; Harding, A. J.; Glen, A.; Taylor, C. S.; Christmas, C. R.; Robinson, P. P.; Rimmer, S.; Boissonade, F. M.; Claeyssens, F.; Haycock, J. W. Nerve Guides Manufactured from Photocurable Polymers to Aid Peripheral Nerve Repair. *Biomaterials* 2015, 49, 77-89. https://doi.org/10.1016/j.biomaterials.2015.01.055.
(13) Lampe, K. J.; Antaris, A. L.; Heilshorn, S. C. Design of Three-Dimensional Engineered Protein Hydrogels for Tailored Control of Neurite Growth. *Acta Biomater.* 2013, 9 (3), 5590-5599. https://doi.org/10.1016/j.actbio.2012.10.033.
(14) Murphy, S. V; Atala, A. 3D Bioprinting of Tissues and Organs. 2014. https://doi.org/10.1038/nbt.2958.
(15) Ong, C. S.; Yesantharao, P.; Huang, C. Y.; Mattson, G.; Boktor, J.; Fukunishi, T.; Zhang, H.; Hibino, N. 3D Bioprinting Using Stem Cells. 2018. https://doi.org/10.1038/pr.2017.252.
(16) Tricomi, B. J.; Dias, A. D.; Corr, D. T. Stem Cell Bioprinting for Applications in Regenerative Medicine. *Ann. N. Y. Acad. Sci.* 2016, 1383 (1), 115-124. https://doi.org/10.1111/nyas.13266.
(17) Jammalamadaka, U.; Tappa, K. Recent Advances in Biomaterials for 3D Printing and Tissue Engineering. *Journal of Functional Biomaterials.* MDPI AG Mar. 1, 2018. https://doi.org/10.3390/jfb9010022.
(18) Kogan, G.; Soltés, L.; Stern, R.; Gemeiner, P. Hyaluronic Acid: A Natural Biopolymer with a Broad Range of Biomedical and Industrial Applications. *Biotechnology Letters.* Springer Jan. 8, 2007, pp 17-25. https://doi.org/10.1007/s10529-006-9219-z.

(19) Highley, C. B.; Prestwich, G. D.; Burdick, J. A. Recent Advances in Hyaluronic Acid Hydrogels for Biomedical Applications. *Current Opinion in Biotechnology*. Elsevier Ltd Aug. 1, 2016, pp 35-40. https://doi.org/10.1016/j.copbio.2016.02.008.

(20) Highley, C. B.; Rodell, C. B.; Burdick, J. A. Direct 3D Printing of Shear-Thinning Hydrogels into Self-Healing Hydrogels. *Adv. Mater.* 2015, 27 (34), 5075-5079. https://doi.org/10.1002/adma.201501234.

(21) Duan, B.; Kapetanovic, E.; Hockaday, L. A.; Butcher, J. T. Three-Dimensional Printed Trileaflet Valve Conduits Using Biological Hydrogels and Human Valve Interstitial Cells. *Acta Biomater.* 2014, 10 (5), 1836-1846. https://doi.org/10.1016/j.actbio.2013.12.005.

(22) Kesti, M.; Müller, M.; Becher, J.; Schnabelrauch, M.; D'Este, M.; Eglin, D.; Zenobi-Wong, M. A Versatile Bioink for Three-Dimensional Printing of Cellular Scaffolds Based on Thermally and Photo-Triggered Tandem Gelation. *Acta Biomater.* 2015, 11 (1), 162-172. https://doi.org/10.1016/j.actbio.2014.09.033.

(23) Suri, S.; Schmidt, C. E. Photopatterned Collagen-Hyaluronic Acid Interpenetrating Polymer Network Hydrogels. *Acta Biomater.* 2009, 5 (7), 2385-2397. https://doi.org/10.1016/j.actbio.2009.05.004.

(24) Spearman, B. S.; Agrawal, N. K.; Rubiano, A.; Simmons, C. S.; Mobini, S.; Schmidt, C. E. Tunable Methacrylated Hyaluronic Acid-Based Hydrogels as Scaffolds for Soft Tissue Engineering Applications. *J. Biomed. Mater. Res. Part A* 2019, 1-13. https://doi.org/10.1002/jbm.a.36814.

(25) Seidlits, S. K.; Khaing, Z. Z.; Petersen, R. R.; Nickels, J. D.; Vanscoy, J. E.; Shear, J. B.; Schmidt, C. E. The Effects of Hyaluronic Acid Hydrogels with Tunable Mechanical Properties on Neural Progenitor Cell Differentiation. *Biomaterials* 2010, 31 (14), 3930-3940. https://doi.org/10.1016/j.biomaterials.2010.01.125.

(26) Ouyang, L.; Yao, R.; Zhao, Y.; Sun, W. Effect of Bioink Properties on Printability and Cell Viability for 3D Bioplotting of Embryonic Stem Cells. *Biofabrication* 2016, 8 (3). https://doi.org/10.1088/1758-5090/8/3/035020.

(27) Zeltz, C.; Gullberg, D. The Integrin-Collagen Connection—a Glue for Tissue Repair? *J. Cell Sci.* 2016, 129 (4), 653-664. https://doi.org/10.1242/jcs.180992.

(28) Zhang, Y. S.; Yue, K.; Aleman, J.; Mollazadeh-Moghaddam, K.; Bakht, S. M.; Yang, J.; Jia, W.; Dell'Erba, V.; Assawes, P.; Shin, S. R.; Dokmeci, M. R.; Oklu, R.; Khademhosseini, A. 3D Bioprinting for Tissue and Organ Fabrication. *Ann. Biomed. Eng.* 2017, 45 (1), 148-163. https://doi.org/10.1007/s10439-016-1612-8.

(29) He, Y.; Yang, F.; Zhao, H.; Gao, Q.; Xia, B.; Fu, J. Research on the Printability of Hydrogels in 3D Bioprinting. *Sci. Rep.* 2016, 6. https://doi.org/10.1038/srep29977.

(30) Chimene, D.; Lennox, K. K.; Kaunas, R. R.; Gaharwar, A. K. Advanced Bioinks for 3D Printing: A Materials Science Perspective. *Annals of Biomedical Engineering*. Springer New York LLC Jun. 1, 2016, pp 2090-2102. https://doi.org/10.1007/s10439-016-1638-y.

(31) Fairbanks, B. D.; Schwartz, M. P.; Bowman, C. N.; Anseth, K. S. Photoinitiated Polymerization of PEG-Diacrylate with Lithium Phenyl-2,4,6-Trimethylbenzoylphosphinate: Polymerization Rate and Cytocompatibility. *Biomaterials* 2009, 30 (35), 6702-6707. https://doi.org/10.1016/j.biomaterials.2009.08.055.

(32) Ouyang, L.; Highley, C. B.; Rodell, C. B.; Sun, W.; Burdick, J. A. 3D Printing of Shear-Thinning Hyaluronic Acid Hydrogels with Secondary Cross-Linking. *ACS Biomater. Sci. Eng.* 2016, 2 (10), 1743-1751. https://doi.org/10.1021/acsbiomaterials.6b00158.

(33) Kiyotake, E. A.; Douglas, A. W.; Thomas, E. E.; Detamore, M. S. Development and Quantitative Characterization of the Precursor Rheology of Hyaluronic Acid Hydrogels for Bioprinting. *Acta Biomater.* 2019, 95, 176-187. https://doi.org/10.1016/j.actbio.2019.01.041.

(34) Poldervaart, M. T.; Goversen, B.; De Ruijter, M.; Abbadessa, A.; Melchels, F. P. W.; Öner, F. C.; Dhert, W. J. A.; Vermonden, T.; Alblas, J. 3D Bioprinting of Methacrylated Hyaluronic Acid (MeHA) Hydrogel with Intrinsic Osteogenicity. *PLoS One* 2017, 12 (6), 1-15. https://doi.org/10.1371/journal.pone.0177628.

(35) Brigham, M. D.; Bick, A.; Lo, E.; Bendali, A.; Burdick, J. A.; Khademhosseini, A. Mechanically Robust and Bioadhesive Collagen and Photocrosslinkable Hyaluronic Acid Semi-Interpenetrating Networks. *Tissue Eng.—Part A* 2009, 15 (7), 1645-1653. https://doi.org/10.1089/ten.tea.2008.0441.

(36) Mazzocchi, A.; Devarasetty, M.; Huntwork, R.; Soker, S.; Skardal, A. Optimization of Collagen Type I-Hyaluronan Hybrid Bioink for 3D Bioprinted Liver Microenvironments. *Biofabrication* 2019, 11, 15003. https://doi.org/10.1088/1758-5090/aae543.

(37) Chang, I. A.; Oh, M.; Kim, M. H.; Park, S.; Kim, B. G.; Namgung, U. Vimentin Phosphorylation by Cdc2 in Schwann Cell Controls Axon Growth via B1-integrin Activation. *FASEB J.* 2012, 26 (6), 2401-2413. https://doi.org/10.1096/fj.11-199018.

(38) Wilson, E. R.; Della-Flora Nunes, G.; Weaver, M. R.; Frick, L. R.; Feltri, M. L. Schwann Cell Interactions during the Development of the Peripheral Nervous System. *Developmental Neurobiology*. John Wiley and Sons Inc. 2020. https://doi.org/10.1002/dneu.22744.

(39) Feltri, M. L.; Porta, D. G.; Previtali, S. C.; Nodari, A.; Migliavacca, B.; Cassetti, A.; Littlewood-Evans, A.; Reichardt, L. F.; Messing, A.; Quattrini, A.; Mueller, U.; Wrabetz, L. Conditional Disruption of 1 Integrin in Schwann Cells Impedes Interactions with Axons. *J. Cell Biol.* 2002, 156 (1), 199-209. https://doi.org/10.1083/jcb.200109021.

(40) Duchi, S.; Onofrillo, C.; O'Connell, C. D.; Blanchard, R.; Augustine, C.; Quigley, A. F.; Kapsa, R. M. I.; Pivonka, P.; Wallace, G.; Di Bella, C.; Choong, P. F. M. Handheld Co-Axial Bioprinting: Application to in Situ Surgical Cartilage Repair. *Sci. Rep.* 2017, 7 (1), 1-12. https://doi.org/10.1038/s41598-017-05699-x.

(41) Nguyen, A. K.; Goering, P. L.; Reipa, V.; Narayan, R. J. Toxicity and Photosensitizing Assessment of Gelatin Methacryloyl-Based Hydrogels Photoinitiated with Lithium Phenyl-2,4,6-Trimethylbenzoylphosphinate in Human Primary Renal Proximal Tubule Epithelial Cells. *Biointerphases* 2019, 14 (2), 021007. https://doi.org/10.1116/1.5095886.

(42) Spearman, B. S.; Desai, V. H.; Mobini, S.; McDermott, M. D.; Graham, J. B.; Otto, K. J.; Judy, J. W.; Schmidt, C. E. Tissue-Engineered Peripheral Nerve Interfaces. *Adv. Funct. Mater.* 2018, 28 (12), 1701713. https://doi.org/10.1002/adfm.201701713.

(43) Cornejo, M.; Nambi, D.; Walheim, C.; Somerville, M.; Walker, J.; Kim, L.; Ollison, L.; Diamante, G.; Vyawahare, S.; De Bellard, M. E. Effect of NRG1, GDNF, EGF and NGF in the Migration of a Schwann Cell Precursor Line. *Neurochem. Res.* 2010, 35 (10), 1643-1651. https://doi.org/10.1007/s11064-010-0225-0.

(44) Lin, Y.-C.; Ramadan, M.; Hronik-Tupaj, M.; Kaplan, D. L.; Philips, B. J.; Sivak, W.; Rubin, J. P.; Marra, K. G.

Spatially Controlled Delivery of Neurotrophic Factors in Silk Fibroin-Based Nerve Conduits for Peripheral Nerve Repair. *Ann. Plast. Surg.* 2011, 67 (2), 147-155. https://doi.org/10.1097/SAP.0b013e3182240346.

(45) Moskowitz, P. F.; Smith, R.; Pickett, J.; Frankfurter, A.; Oblinger, M. M. Expression of the Class III β-Tubulin Gene during Axonal Regeneration of Rat Dorsal Root Ganglion Neurons. *J. Neurosci. Res.* 1993, 34 (1), 129-134. https://doi.org/10.1002/jnr.490340113.

(46) Santos, D.; Gonzalez-Perez, F.; Navarro, X.; Valle, J. del. Dose-Dependent Differential Effect of Neurotrophic Factors on In Vitro and In Vivo Regeneration of Motor and Sensory Neurons. *Neural Plast.* 2016, 2016. https://doi.org/10.1155/2016/4969523.

(47) Fine, E. G.; Decosterd, I.; Papaloïzos, M.; Zurn, A. D.; Aebischer, P. GDNF and NGF Released by Synthetic Guidance Channels Support Sciatic Nerve Regeneration across a Long Gap. *Eur. J. Neurosci.* 2002, 15 (4), 589-601. https://doi.org/10.1046/j.1460-9568.2002.01892.x.

(48) Kemp, S. W. P.; Cederna, P. S.; Midha, R. Comparative Outcome Measures in Peripheral Regeneration Studies. *Exp. Neurol.* 2017, 287, 348-357. https://doi.org/10.1016/j.expneurol.2016.04.011.

(49) Gomez, N.; Chen, S.; Schmidt, C. E. Polarization of Hippocampal Neurons with Competitive Surface Stimuli: Contact Guidance Cues Are Preferred over Chemical Ligands. *J. R. Soc. Interface* 2007, 4 (13), 223-233. https://doi.org/10.1098/rsif.2006.0171.

(50) Bhattacharjee, T.; Zehnder, S. M.; Rowe, K. G.; Jain, S.; Nixon, R. M.; Sawyer, W. G.; Angelini, T. E. Writing in the Granular Gel Medium. *Sci. Adv.* 2015, 1 (8), e1500655. https://doi.org/10.1126/sciadv.1500655.

(51) Johnson, B. N.; Lancaster, K. Z.; Zhen, G.; He, J.; Gupta, M. K.; Kong, Y. L.; Engel, E. A.; Krick, K. D.; Ju, A.; Meng, F.; Enquist, L. W.; Jia, X.; McAlpine, M. C. 3D Printed Anatomical Nerve Regeneration Pathways. *Adv. Funct. Mater.* 2015, 25 (39), 6205-6217. https://doi.org/10.1002/adfm.201501760.

(52) Alluin, O.; Wittmann, C.; Marqueste, T.; Chabas, J. F.; Garcia, S.; Lavaut, M. N.; Guinard, D.; Feron, F.; Decherchi, P. Functional Recovery after Peripheral Nerve Injury and Implantation of a Collagen Guide. *Biomaterials* 2009, 30 (3), 363-373. https://doi.org/10.1016/j.biomaterials.2008.09.043.

(53) Jansen, K.; Van Der Werff, J. F. A.; Van Wachem, P. B.; Nicolai, J. P. A.; De Leij, L. F. M. H.; Van Luyn, M. J. A. A Hyaluronan-Based Nerve Guide: In Vitro Cytotoxicity, Subcutaneous Tissue Reactions, and Degradation in the Rat. *Biomaterials* 2004, 25 (3), 483-489. https://doi.org/10.1016/S0142-9612(03)00544-1.

(54) Leach, J. B.; Schmidt, C. E. Characterization of Protein Release from Photocrosslinkable Hyaluronic Acid-Polyethylene Glycol Hydrogel Tissue Engineering Scaffolds. *Biomaterials* 2005, 26 (2), 125-135. https://doi.org/10.1016/j.biomaterials.2004.02.018.

(55) Bittner, S. M.; Guo, J. L.; Mikos, A. G. Spatiotemporal Control of Growth Factors in Three-Dimensional Printed Scaffolds. *Bioprinting.* Elsevier B. V. Dec. 1, 2018, p e00032. https://doi.org/10.1016/j.bprint.2018.e00032.

(56) Cao, X.; Shoichet, M. S. Defining the Concentration Gradient of Nerve Growth Factor for Guided Neurite Outgrowth. *Neuroscience* 2001, 103 (3), 831-840. https://doi.org/10.1016/S0306-4522(01)00029-X.

(57) Omura, T.; Sano, M.; Omura, K.; Hasegawa, T.; Doi, M.; Sawada, T.; Nagano, A. Different Expressions of BDNF, NT3, and NT4 in Muscle and Nerve after Various Types of Peripheral Nerve Injuries. *J. Peripher. Nerv. Syst.* 2005, 10 (3), 293-300. https://doi.org/10.1111/j.1085-9489.2005.10307.x.

(58) Johnson, B. N.; Jia, X. 3D Printed Nerve Guidance Channels: Computer-Aided Control of Geometry, Physical Cues, Biological Supplements and Gradients. *Neural Regen. Res.* 2016, 11 (10), 1568-1569. https://doi.org/10.4103/1673-5374.193230.

(59) Xu, H.; Holzwarth, J. M.; Yan, Y.; Xu, P.; Zheng, H.; Yin, Y.; Li, S.; Ma, P. X. Conductive PPY/PDLLA Conduit for Peripheral Nerve Regeneration. *Biomaterials* 2014, 35 (1), 225-235. https://doi.org/10.1016/j.biomaterials.2013.10.002.

(60) Huang, J.; Hu, X.; Lu, L.; Ye, Z.; Zhang, Q.; Luo, Z. Electrical Regulation of Schwann Cells Using Conductive Polypyrrole/Chitosan Polymers. *J. Biomed. Mater. Res.—Part A* 2010, 93 (1), 164-174. https://doi.org/10.1002/jbm.a.32511.

(61) Abidian, M. R.; Daneshvar, E. D.; Egeland, B. M.; Kipke, D. R.; Cederna, P. S.; Urbanchek, M. G. Hybrid Conducting Polymer-Hydrogel Conduits for Axonal Growth and Neural Tissue Engineering. *Adv. Healthc. Mater.* 2012, 1 (6), 762-767. https://doi.org/10.1002/adhm.201200182.

(62) Arce, S. H. The Multidisciplinary Perspective of Cell Shape, University of Florida, 2014.

We claim:

1. A three-dimensional (3D), bioprinted competitive test bed, the test bed comprising:

a central section comprising a base hydrogel material and living cells within the base hydrogel material;

a first arm portion directly adjacent the central section, the first arm portion comprising the base hydrogel material and a first test compound within the base hydrogel material; and a second arm portion directly adjacent the central section and separated from the first arm portion by the central section, the second arm portion comprising the base hydrogel material and a second test compound, other test stimulus, or a combination thereof, within the base hydrogel material, wherein the base hydrogel material for the central portion and each arm portion comprises a crosslinked biocompatible hydrogel matrix material in the form of a 3D hydrogel scaffold and wherein the base hydrogel material further comprises an extracellular matrix (ECM) component crosslinked with the hydrogel matrix material in the form of a 3D hydrogel scaffold;

wherein the 3D hydrogel scaffold is formed by bioprinting a base bioink composition comprising the ECM component, the hydrogel matrix material, and a photoinitiator capable of crosslinking the hydrogel matrix material and the ECM component and loading the base bioink composition in an extrusion-based 3D bioprinter and allowing partial gelation of the bioink at 37° C. for 10 minutes before printing;

wherein the crosslinked biocompatible hydrogel matrix material consists of a multi-component methacrylated hyaluronic acid (MeHA)-based hydrogel, the multi-component MeHA-based hydrogel comprising: an MeHA component and the extracellular matrix (ECM) component, wherein the MeHA component and the ECM component are crosslinked in the form of a 3D hydrogel scaffold;

wherein the MeHA component is methacrylic anhydride HA (MAHA), wherein the ECM component is collagen; and wherein MAHA-derived components have a concentration of about 10-20 mg/mL and collagen-derived components have a concentration of about 0.1-50 mg/ml in the crosslinked biocompatible hydrogel matrix.

2. The 3D bioprinted test bed of claim 1, wherein the base hydrogel material further comprises a growth medium or one or more growth factors within the hydrogel material.

3. The 3D bioprinted test bed of claim 1, wherein one or more of the first test compound and second compound are selected from: growth factors, small molecule drugs, biomolecules, and other bioactive agents.

4. The 3D bioprinted test bed of claim 1, wherein the cells are neural cells.

5. The 3D bioprinted test bed of claim 4, wherein the cells are dorsal root ganglia.

6. The 3D bioprinted test bed of claim 1, wherein the cells in the central portion have a density of about $10^4$ to $10^7$ cells/mL when the 3D bioprinted test bed is printed.

7. The 3D bioprinted test bed of claim 1, further comprising one or more additional arm portions, each additional arm portion positioned directly adjacent the central section and separated from the first and second arm portions by the central section, each additional arm portion comprising the base hydrogel material and having a test compound, other test stimulus, or a combination thereof, wherein the test compound, test stimulus or combination is different in each arm portion.

8. The 3D bioprinted test bed of claim 1, wherein the other test stimulus in the second arm portion is a physical stimulus included in the base hydrogel material of the second arm portion, wherein the physical stimulus is selected from the group of physical stimuli consisting of: a microarchitectural feature, a density gradient, and support cells.

9. The 3D bioprinted test bed of claim 1, wherein the arm portions do not have any cells in the base material when the 3D bioprinted test bed is printed, and wherein the 3D bioprinted test bed is configured such that cells can migrate, grow, or proliferate to the arm portions in response to the first test compound, second test compound, or other test stimulus, or a combination thereof.

10. A three-dimensional (3D), bioprinted cell scaffold, the cell scaffold comprising:
 a multi-component methacrylated hyaluronic acid (MeHA)-based hydrogel, the hydrogel consisting of: an MeHA component and an extracellular matrix (ECM) component, wherein the MeHA component and ECM component are crosslinked to create a 3D hydrogel scaffold; the scaffold further comprising at least one population of living cells seeded within the 3D hydrogel scaffold, and two or more test compounds; wherein the cells and each of the test compounds are located in different portions of the 3D bioprinted cell scaffold when the cell scaffold is printed;
 wherein the MeHA component is methacrylic anhydride HA (MAHA), wherein the ECM component is collagen; and wherein MAHA-derived components have a concentration of about 10-20 mg/mL and collagen-derived components have a concentration of about 0.1-50 mg/mL in the hydrogel scaffold.

11. A method of comparatively testing the effect of one or more test compounds on cell growth behavior, the method comprising:
 providing a 3D bioprinted test bed of claim 1, wherein the cells are in the central portion and wherein the first arm portion contains a first test compound and the second arm portion contains an optional second test compound, an optional test stimulus, or no additional compounds or stimuli;
 culturing the 3D bioprinted test bed; and
 quantitatively comparing cell growth behavior of cells in the central portion towards each arm portion to determine if the first test compound, optional second test compound, or optional test stimulus has an effect on one or more cell growth behaviors selected from the group consisting of: cell growth, cell proliferation, cell migration, and neurite extension, measurement of secreted protein products, measurement of cellular electrical activity, and measurement of protein/gene expression.

12. The method of claim 11, wherein the second arm comprises a second test compound and wherein the first test compound and the second test compound are independently selected from the group consisting of: growth factors, small molecule drugs, biomolecules, and other bioactive agents.

13. The method of claim 11, wherein the second arm contains a test stimulus selected from the group of physical stimuli consisting of: a physical obstacle, a density gradient, and the presence of support cells.

14. The method of claim 11, wherein the 3D bioprinted test bed comprises 3 or more arms each containing a different test compound or test stimuli, and wherein one of the arms can optionally contain no test compound or test stimuli as a negative control.

15. The method of claim 11, wherein the living cells are neural cells and wherein at least one cell growth behavior comprises neurite extension.

* * * * *